United States Patent
Pavel et al.

(10) Patent No.: US 11,426,423 B2
(45) Date of Patent: Aug. 30, 2022

(54) METHODS RELATING TO LUNG CANCER

(71) Applicant: Trustees of Boston University, Boston, MA (US)

(72) Inventors: Ana Brandusa Pavel, New York, NY (US); Joshua David Campbell, Sharon, MA (US); Marc Elliott Lenburg, Brookline, MA (US); Avrum Elliot Spira, Newton, MA (US)

(73) Assignee: Trustees of Boston University, Boston, MA (US)

( * ) Notice: Subject to any disclaimer, the term of this patent is extended or adjusted under 35 U.S.C. 154(b) by 0 days.

(21) Appl. No.: 16/828,053

(22) Filed: Mar. 24, 2020

(65) Prior Publication Data

US 2020/0222446 A1 Jul. 16, 2020

Related U.S. Application Data

(60) Division of application No. 16/391,473, filed on Apr. 23, 2019, now Pat. No. 10,632,140, which is a continuation of application No. 15/877,447, filed on Jan. 23, 2018, now Pat. No. 10,314,855.

(60) Provisional application No. 62/449,223, filed on Jan. 23, 2017.

(51) Int. Cl.
*C07H 21/04* (2006.01)
*A61K 31/7105* (2006.01)
*G01N 33/574* (2006.01)
*A61P 35/00* (2006.01)
*C12Q 1/6825* (2018.01)
*C12Q 1/6886* (2018.01)

(52) U.S. Cl.
CPC .......... *A61K 31/7105* (2013.01); *A61P 35/00* (2018.01); *C12Q 1/6825* (2013.01); *C12Q 1/6886* (2013.01); *G01N 33/57423* (2013.01); *C12Q 2539/10* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| 2010/0179213 | A1 | 7/2010 | Patrawala et al. | |
|---|---|---|---|---|
| 2013/0053275 | A1 | 2/2013 | Knudsen | |
| 2015/0080243 | A1* | 3/2015 | Whitney | G16B 20/00 506/9 |
| 2016/0108405 | A1 | 4/2016 | Sozzi et al. | |
| 2016/0251720 | A1* | 9/2016 | Schulze | C12Q 1/6883 514/44 A |

FOREIGN PATENT DOCUMENTS

| EP | 2327800 A1 | 6/2011 |
|---|---|---|
| EP | 2502630 A2 | 9/2012 |
| WO | 2013049152 A2 | 4/2013 |

OTHER PUBLICATIONS

Gesthalter et al. ("Translating the transcriptome into tools for the early detection and prevention of lung cancer." Thorax 70.5 (2015): 476-481).*
Wang et al. "Effect and molecular mechanism of mir-146a on proliferation of lung cancer cells by targeting and regulating MIF gene." Asian Pacific Journal of Tropical Medicine 9(8): 806-811 (2016).
Yanaihara et al. "Unique microRNA molecular profiles in lung cancer diagnosis and prognosis." Cancer Cell 9(3): 189-198 (2006).
Beane et al., "A prediction model for lung cancer diagnosis that integrates genomic and clinical features." Cancer Prevention Research 1(1):56-64 (2008).
Berindan-Neagoe et al., "Molecular pathways: microRNAs, cancer cells, and microenvironment" Clinical Cancer Research 20(24):6247-6253 (2014).
Bhaumik et al., "MicroRNAs miR-146a/b negatively modulate the senescence-associated inflammatory mediators IL-6 and IL-8." Aging (Albany NY) 1(4):402-411 (2009).
Brase et al., "Serum microRNAs as non-invasive biomarkers for cancer." Molecular cancer 9(1):306 (2010).
Campbell et al., "Assessment of microRNA differential expression and detection in multiplexed small RNA sequencing data." RNA 21(2):164-171 (2015).
Catuogno et al., "miR-34c may protect lung cancer cells from paclitaxel-induced apoptosis" Oncogene 32(3):341-351 (2013).
Chen et al., "miR-146a inhibits cell growth, cell migration and induces apoptosis in non-small cell lung cancer cells" PloS One 8(3):e60317 (2013).
Chou et al. "EGFR promotes lung tumorigenesis by activating miR-7 through a Ras/ERK/Myc pathway that targets the Ets2 transcriptional repressor ERF." Cancer research 70(21):8822-8831 (2010).
Franklin et al., "Widely dispersed p53 mutation in respiratory epithelium. A novel mechanism for field carcinogenesis." Journal of Clinical Investigation 100(8):2133-2137 (1997).
Guo et al., "Promoter hypermethylation of resected bronchial margins." Clinical Cancer Research 10(15):5131-5136 (2004).
Gupta et al. "Smoking intensity, oxidative stress and chemotherapy in non-small cell lung cancer: A correlated prognostic study." BioScience Trends 3(5): 191-199 (2009).
Huang et al., "Systematic and integrative analysis of large gene lists using DAVID bioinformatics resources." Nature Protocols 4(1):44-57 (2009).
Huang et al. "Two MicroRNA Panels to Discriminate Three Subtypes of Lung Carcinoma in Bronchial Brushing Specimens." American Journal of Respiratory and Critical Care Medicine 186(11): 1160-1167 (2012).

(Continued)

*Primary Examiner* — Kimberly Chong
(74) *Attorney, Agent, or Firm* — Nixon Peabody LLP; Ronald I. Eisenstein; Nicole D. Kling

(57) ABSTRACT

The methods and assays described herein relate to detection, diagnosis, and treatment of lung cancer, e.g., by detecting the level of expression of certain miRNAs described herein and/or by therapeutically increasing the level of those miRNAs.

10 Claims, 4 Drawing Sheets

Specification includes a Sequence Listing.

(56) References Cited

OTHER PUBLICATIONS

Jiang et al. "MiR-125b promotes proliferation and migration of type II endometrial carcinoma cells through targeting TP53INP1 tumor suppressor in vitro and in vivo." BMC Cancer 11(1):425 (2011).
Kim et al., "Cancer survival classification using integrated data sets and intermediate information." Artificial intelligence in medicine 62(1):23-31 (2014).
Krysan et al. "PGE2-driven expression of c-Myc and oncomiR-17-92 contributes to apoptosis resistance in NSCLC." Molecular Cancer Research 12(5):765-774 (2014).
Kumaraswamy et al., "BRCA1 regulation of epidermal growth factor receptor (EGFR) expression in human breast cancer cells involves microRNA-146a and is critical for its tumor suppressor function." Oncogene 34(33):4333-4346 (2015).
Labbaye et al., "The emerging role of MIR-146A in the control of hematopoiesis, immune function and cancer." Journal of hematology & oncology 5(1):13 (2012).
Lammers et al., "Drug targeting to tumors: principles, pitfalls and (pre-) clinical progress." Journal of Controlled Release 161(2):175-187 (2012).
Li et al., "MicroRNA-324-3p regulates nasopharyngeal carcinoma radioresistance by directly targeting WNT2B." European Journal of Cancer 49(11):2596-2607 (2013).
Li et al., "MiR-146a-5p inhibits cell proliferation and cell cycle progression in NSCLC cell lines by targeting CCND1 and CCND2." Oncotarget 7(37):59287 (2016).
Lu et al., "MicroRNA expression profiles classify human cancers." Nature 435(7043):834-838 (2005).
Mitchell et al., "Circulating microRNAs as stable blood-based markers for cancer detection." Proceedings of the National Academy of Sciences 105(30):10513-10518 (2008).
Miyazu et al., "Telomerase expression in noncancerous bronchial epithelia is a possible marker of early development of lung cancer." Cancer Research 65(21):9623-9627 (2005).
Nian et al. "miR-223 functions as a potent tumor suppressor of the Lewis lung carcinoma cell line by targeting insulin-like growth factor-1 receptor and cyclin-dependent kinase 2." Oncology letters 6(2): 359-366 (2013).
Nygaard et al., "Identification and analysis of miRNAs in human breast cancer and teratoma samples using deep sequencing." BMC medical genomics 2(1):35 (2009).

Pavel et al., "microRNA expression in bronchial epithelium for lung cancer detection." AACR 76(14):1954 (2016) [ABSTRACT].
Perdomo et al., "MicroRNA 4423 is a primate-specific regulator of airway epithelial cell differentiation and lung carcinogenesis." PNAS110(47):18946-18951 (2013).
Powell et al., "Loss of heterozygosity in epithelial cells obtained by bronchial brushing: clinical utility in lung cancer." Clinical Cancer Research 5(8):2025-2034 (1999).
Robles et al. "An integrated prognostic classifier for stage I lung adenocarcinoma based on mRNA, microRNA, and DNA methylation biomarkers." Journal of Thoracic Oncology 10(7): 1037-1048 (2015).
Schembri et al. "MicroRNAs as modulators of smoking-induced gene expression changes in human airway epithelium." PNAS 106(7):2319-2324 (2009).
Shen et al., "Plasma microRNAs as potential biomarkers for non-small-cell lung cancer." Laboratory investigation 91(4):579-587 (2011).
Silvestri et al., "A bronchial genomic classifier for the diagnostic evaluation of lung cancer." New England Journal of Medicine 373(3):243-251 (2015).
Spira et al., "Airway epithelial gene expression in the diagnostic evaluation of smokers with suspect lung cancer." Nature Medicine 13(3):361-366 (2007).
Spira et al., "Effects of cigarette smoke on the human airway epithelial cell transcriptome." PNAS 101(27):10143-10148 (2004).
Sridhar et al. "Smoking-induced gene expression changes in the bronchal airway are reflected in nasal and buccal epithelium." BMC Genomics 9(1): 259 pp. 1-13 (2008).
Taylor et al., "MicroRNA signatures of tumor-derived exosomes as diagnostic biomarkers of ovarian cancer." Gynecologic Oncology 110(1):13-21 (2008).
Whitney et al., "Derivation of a bronchial genomic classifier for lung cancer in a prospective study of patients undergoing diagnostic bronchoscopy." BMC medical genomics 8(1):18 (2015).
Wistuba et al., "Molecular damage in the bronchial epithelium of current and former smokers." Journal of the National Cancer Institute 89(18):1366-1373 (1997).
Wu et al. "Serum Levels of miR-19b and miR-146a as Prognostic Biomarkers for Non-Small Cell Lung Cancer." Tohoku J. Exp. Med. 232(2): 85-95 (2014).
Zheng et al. "Plasma microRNAs as novel biomarkers for early detection of lung cancer." Int J Clin Exp Pathol 4(6):575-586 (2011).

* cited by examiner

METHODS RELATING TO LUNG CANCER

CROSS-REFERENCE TO RELATED APPLICATIONS

This application is a divisional under 35 U.S.C. § 121 of co-pending U.S. application Ser. No. 16/391,473 filed Apr. 23, 2019, which is a continuation under 35 U.S.C. § 120 of U.S. Application Ser. No. 15/877,447 filed Jan. 23, 2018 issued as U.S. Pat. No. 10,314,855 on Jun. 11, 2019, which claims benefit under 35 U.S.C. § 119(e) of U.S. Provisional Application No. 62/449,223 filed Jan. 23, 2017, the contents of which are incorporated herein by reference in their entireties.

GOVERNMENT SUPPORT

This invention was made with government support under Grant Nos. CA152751 and CA214182 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jan. 22, 2018, is named 701586-088722-US_SL.txt and is 2,933 bytes in size.

BACKGROUND

World-wide, lung cancer is one of the most frequently-occurring types of cancer and is a leading cause of cancer-related mortality. Over 1.8 million new cases are diagnosed each year, while 1.56 million individual die due to lung cancer annually. Lung cancer remains the leading cause of cancer-related death in the United States and the world due, in large part, to the inability to detect the disease at its earliest and curable stage. Development of improved diagnostics and therapeutics is critical to providing improved care for lung cancer patients.

SUMMARY

By analyzing the lungs of lung cancer patients, it was found that certain microRNAs (miRNAs) were found to be under-expressed in lung cancer and are demonstrated to act as tumor suppressors in non-cancerous tissue. Accordingly, expression of these miRNAs is diagnostic of the presence of lung cancer in a patient, and methods of increasing the expression of these miRNAs can be therapeutic.

In one aspect of any of the embodiments, described herein is a method of treating lung cancer in a subject in need thereof, the method comprising administering to the subject an agonist of at least 1 miRNA selected from the group consisting of: miR-146a-5p, miR-324-5p, miR-223-3p, miR-223-5p; miR-450b-5p, miR-221-3p-miR-505-3p, and miR-582-5p to the subject. In one aspect of any of the embodiments, described herein is a method of treating lung cancer in a subject in need thereof, the method comprising administering to the subject an agonist of at least 1 miRNA selected from Table 10 and/or an inhibitor of at least 1 miRNA selected from Table 11 to the subject. In some embodiments of any of the aspects, the administering step comprises the administration of a vector comprising a nucleic acid encoding the agonist and/or inhibitor.

In one aspect of any of the embodiments, described herein is a method comprising: detecting the level of expression of at least 1 miRNA selected from the group consisting of: miR-146a-5p, miR-324-5p, miR-223-3p, miR-223-5p; miR-450b-5p, miR-221-3p-miR-505-3p, and miR-582-5p; in a sample obtained from a subject. In one aspect of any of the embodiments, described herein is a method comprising: obtaining a sample from a subject; and detecting the level of expression of at least 1 miRNAs selected from the group consisting of: miR-146a-5p, miR-324-5p, miR-223-3p, miR-223-5p; miR-450b-5p, miR-221-3p-miR-505-3p, and miR-582-5p; in the sample.

In one aspect of any of the embodiments, described herein is a method comprising: detecting the level of expression of at least 1 miRNA selected from Table 10 and/or Table 11 in a sample obtained from a subject. In one aspect of any of the embodiments, described herein is a method comprising: obtaining a sample from a subject; and detecting the level of expression of at least 1 miRNA selected from Table 10 and/or Table 11 in the sample.

In one aspect of any of the embodiments, described herein is an assay for detecting lung cancer a subject, the assay comprising: subjecting a test sample of a subject to at least one analysis to determine the level of expression of at least 1 miRNAs selected from the group consisting of: miR-146a-5p, miR-324-5p, miR-223-3p, miR-223-5p; miR-450b-5p, miR-221-3p-miR-505-3p, and miR-582-5p; wherein an expression level of the at least 1 miRNA which decreased relative to a reference level, indicates the presence of lung cancer. In one aspect of any of the embodiments, described herein is an assay for detecting lung cancer a subject, the assay comprising: subjecting a test sample of a subject to at least one analysis to determine the level of expression of at least 1 miRNA selected from Table 10 and/or Table 11; wherein an expression level of the at least 1 miRNA of Table 10 which is decreased relative to a reference level or an expression level of the at least 1 miRNA of Table 11 which is increased relative to a reference level, indicates the presence of lung cancer.

In one aspect of any of the embodiments, described herein is a method of treating lung cancer in a subject in need thereof, the method comprising administering to the subject an agonist of at least 1 miRNA selected from Table 10 or an inhibitor of at least 1 miRNA selected from Table 11 to the subject. In some embodiments of any of the aspects, the subject is administered an agonist of at least 1 miRNA selected from the group consisting of: miR-146a-5p, miR-324-5p, miR-223-3p, miR-223-5p; miR-450b-5p, miR-221-3p-miR-505-3p, and miR-582-5p. In some embodiments of any of the aspects, the administering step comprises the administration of a vector comprising a nucleic acid encoding the agonist and/or inhibitor.

In some embodiments of any of the aspects, the level of expression is detected for at least two miRNAs selected from the group consisting of: miR-146a-5p, miR-324-5p, miR-223-3p, miR-223-5p; miR-450b-5p, miR-221-3p-miR-505-3p, and miR-582-5p. In some embodiments of any of the aspects, the level of expression is detected for at least three miRNAs selected from the group consisting of: miR-146a-5p, miR-324-5p, miR-223-3p, miR-223-5p; miR-450b-5p, miR-221-3p-miR-505-3p, and miR-582-5p. In some embodiments of any of the aspects, the level of expression is detected for at least four miRNAs selected from the group consisting of: miR-146a-5p, miR-324-5p, miR-223-3p, miR-223-5p; miR-450b-5p, miR-221-3p-miR-505-3p, and miR-582-5p. In some embodiments of any of the aspects, the level of expression is detected for at least five miRNAs selected from the group consisting of: miR-146a-5p, miR-324-5p, miR-223-3p, miR-223-5p; miR-450b-5p, miR-221-3p-miR-505-3p, and miR-582-5p. In some embodiments of any of the aspects, the level of expression is detected for at least six miRNAs selected from the group consisting of: miR-146a-5p, miR-324-5p, miR-223-3p, miR-223-5p; miR-450b-5p, miR-221-3p-miR-505-3p, and miR-582-5p. In some embodiments of any of the aspects, the level of expression is detected for at least seven miRNAs selected from the group consisting of: miR-146a-5p, miR-324-5p, miR-223-3p, miR-223-5p; miR-450b-5p, miR-221-3p-miR-505-3p, and miR-582-5p. In some embodiments of any of the aspects, the level of expression is detected for miR-146a-5p, miR-324-5p, miR-223-3p, miR-223-5p; miR-450b-5p, miR-221-3p-miR-505-3p, and miR-582-5p. In some embodiments of any of the aspects, the level of expression is detected for at least miR-146a-5p, miR-324-5p, miR-223-3p, and miR-223-5p. In some embodiments of any of the aspects, the level of expression is detected for at least miR-146a-5p.

In some embodiments of any of the aspects, the subject is a mammal. In some embodiments of any of the aspects, the subject is a human. In some embodiments of any of the aspects, the subject is a current or former smoker. In some embodiments of any of the aspects, the sample is a bronchial brushing or nose epithelial sample. In some embodiments of any of the aspects, the subject is at risk of developing lung cancer.

In some embodiments of any of the aspects, the detecting step comprises sequencing of miRNAs in the sample. In some embodiments of any of the aspects, the method further comprises detecting the expression level of one or more mRNAs. In some embodiments of any of the aspects, the expression level of no more than 100 miRNAs and/or mRNAs is detected.

In some embodiments of any of the aspects, the method further comprises administering an agonist of at least 1 miRNA selected from Table 10 or an inhibitor of at least one miRNA selected from Table 11 to the subject. In some embodiments of any of the aspects, the method further comprises administering an agonist of at least 1 miRNA selected from the group consisting of: miR-146a-5p, miR-324-5p, miR-223-3p, miR-223-5p; miR-450b-5p, miR-221-3p-miR-505-3p, and miR-582-5p to the subject.

BRIEF DESCRIPTION OF THE DRAWINGS

FIG. 2A depicts expression of hsa-miR146a-5p (P=0.0008, q=0.125). FIG. 2B depicts expression of hsa-miR-324-5p (P=0.0007, q=0.125). FIG. 2C depicts expression of hsa-miR-223-3p (P=0.0007, q=0.125). FIG. 2D depicts expression of hsa-miR-223-5p (P=0.0016, q=0.184).

FIG. 4 depicts a graph of significantly differentially expressed microRNAs between current and former smokers (q<0.01). Some of these microRNAs have been previously associated with smoking status, such as miR-218, miR-365, miR-30 and miR-99a.

DETAILED DESCRIPTION

Figure 1:
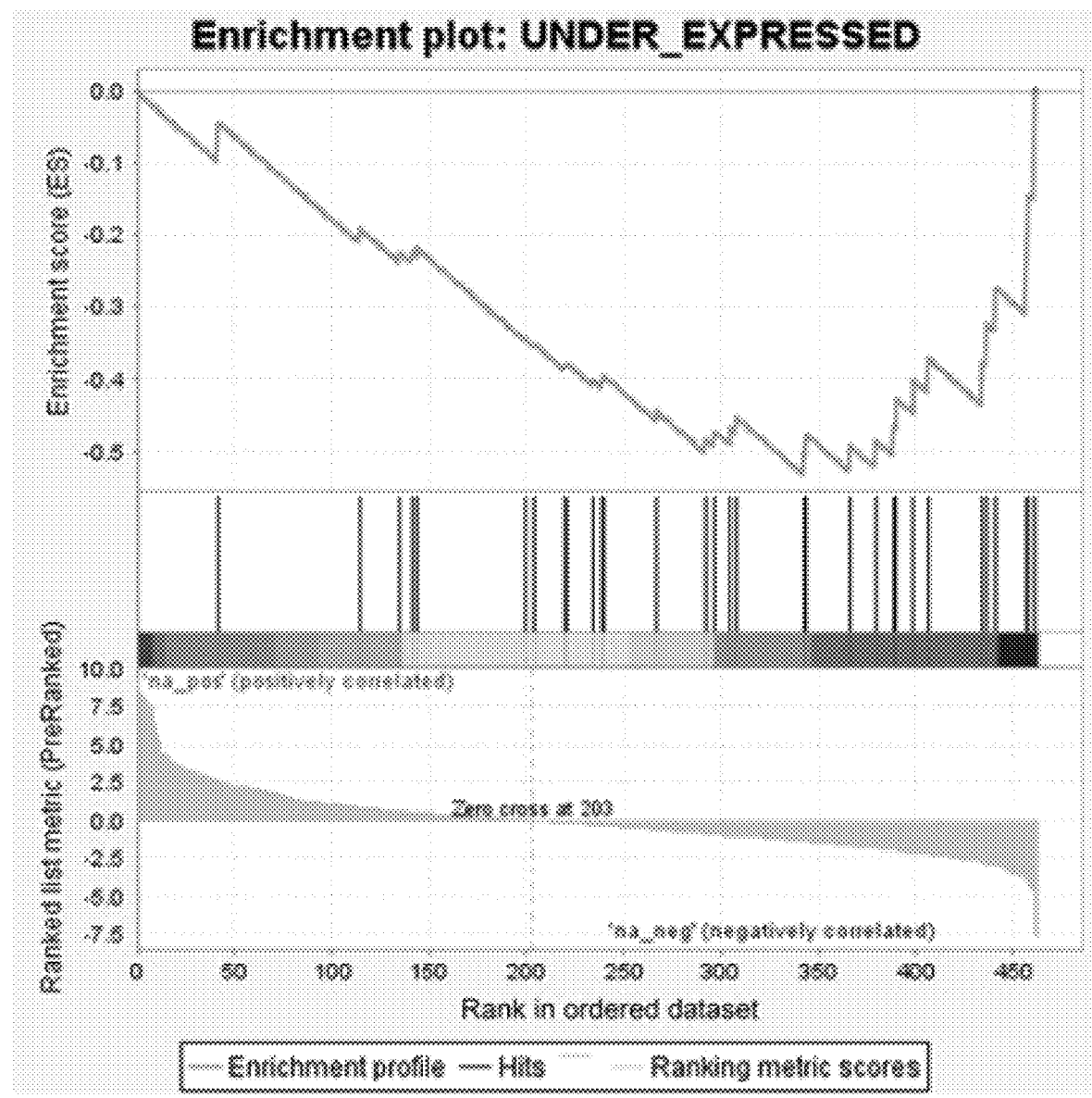
FIG. 1 depicts the enrichment of known smoking-related miRNAs by GSEA. A set of 23 miRNAs that are expressed at lower levels in bronchial airway samples from current smokers are significantly enriched among the miRNAs most repressed among current smokers in the current dataset (q<0.001). The bar below the graph shows all 463 miRNAs ranked from most induced in smokers to most repressed (as shown in the distribution oft statistics at the bottom), while the vertical black lines show the position, within this ranked list, of the 23 miRNAs described above to have decreased expression in the bronchial airway of smokers. The running enrichment score, which has a significantly negative minimum, indicates that the 23 miRNAs are among the miRNA most repressed among current smokers in the current small RNA sequencing dataset.
Figure 2A:
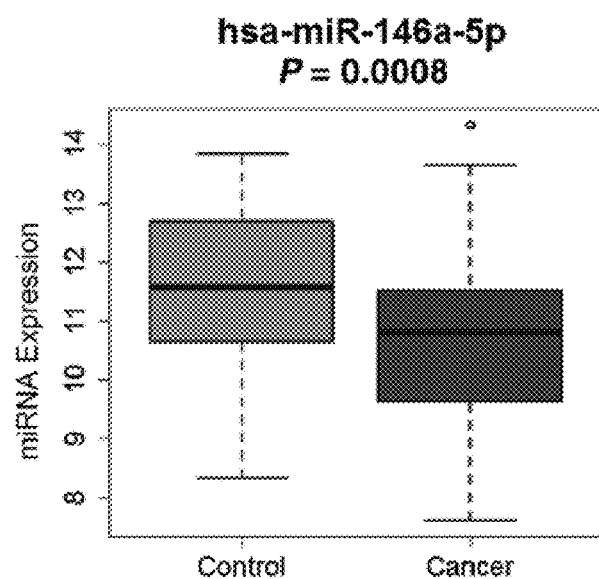
FIGS. 2A-2D depict miRNAs significantly differentially expressed in bronchial epithelium between patients with and without lung cancer.
Figure 2B:
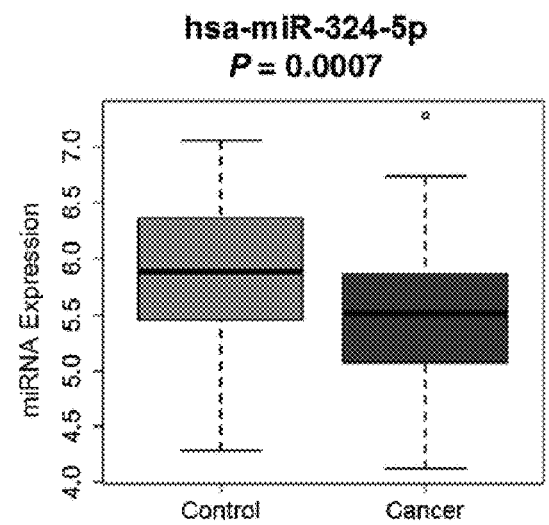
Figure 2C:
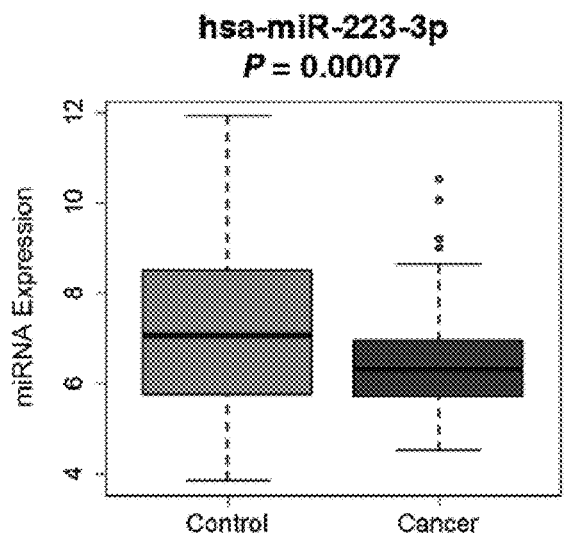
Figure 2D:
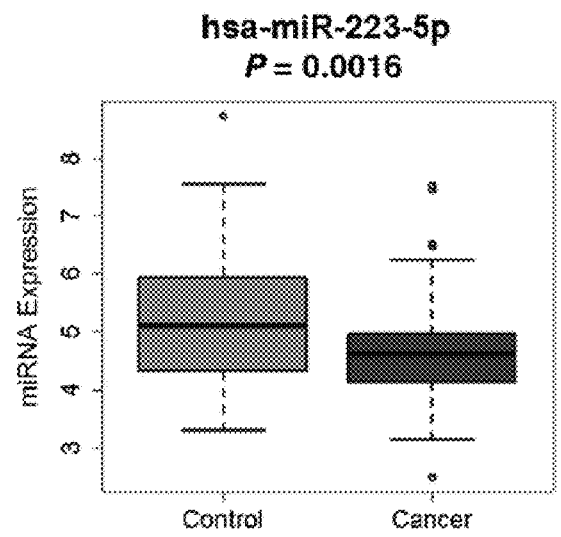
Figures 3A, 3B:
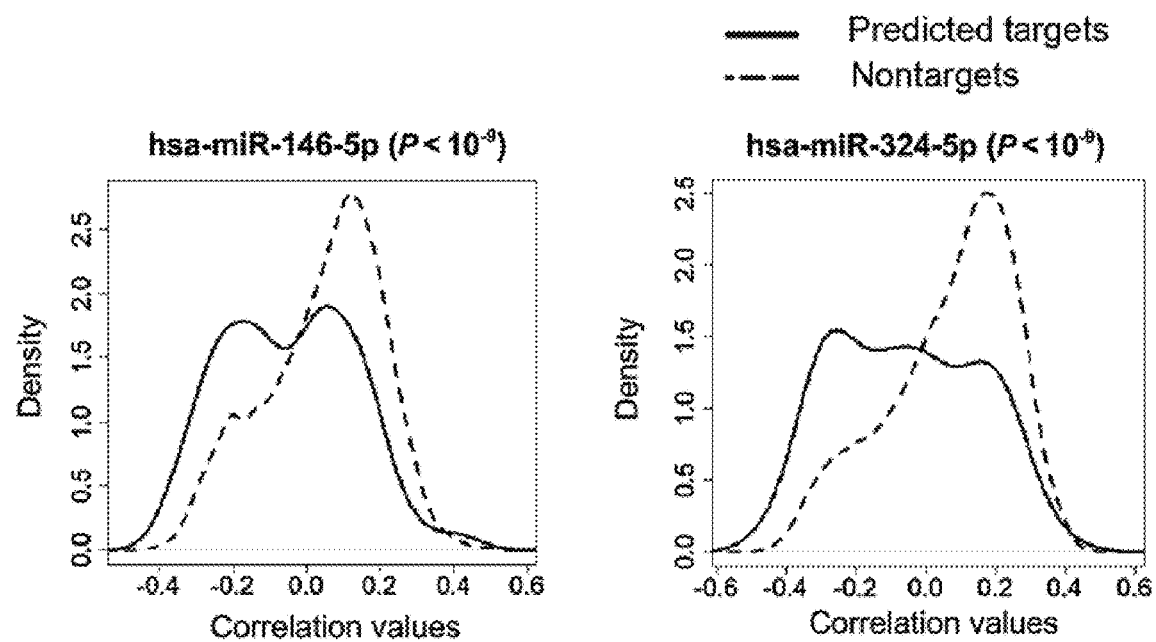
FIGS. 3A-3D demonstrate that miRNAs with cancer-associated expression are negatively correlated with their predicted targets. The distribution of miRNA-mRNA correlations for each miRNA and its predicted targets is shown with a solid line. The null distribution of miRNA-mRNA correlations for each miRNA and all nontargets is shown with a dashed line. The difference between the two distributions was tested using the Kolmogorov-Smirnov test.
Figures 3C, 3D:
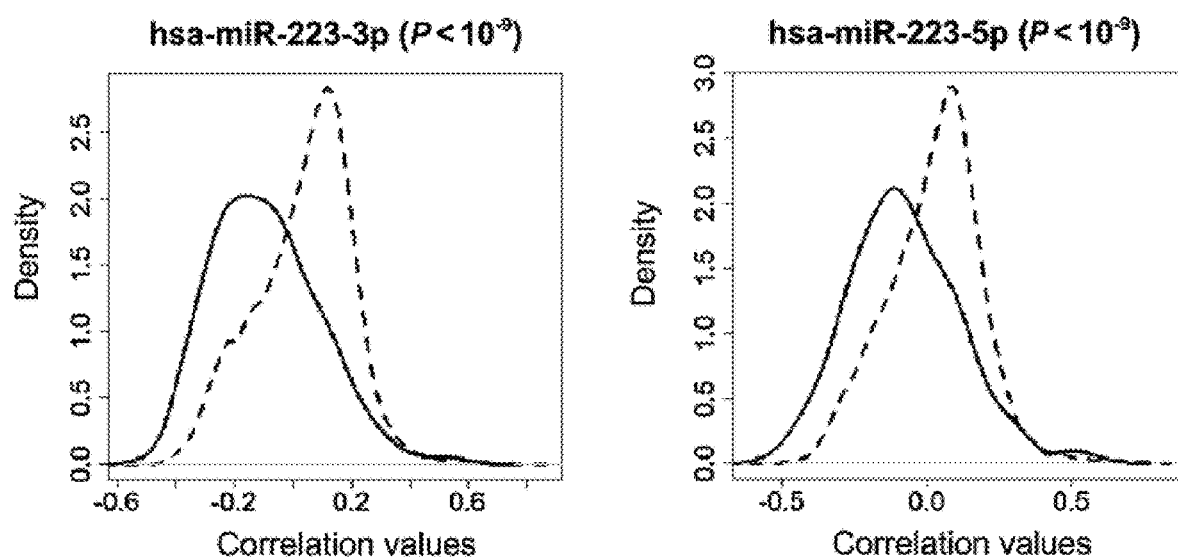
Figure 4:
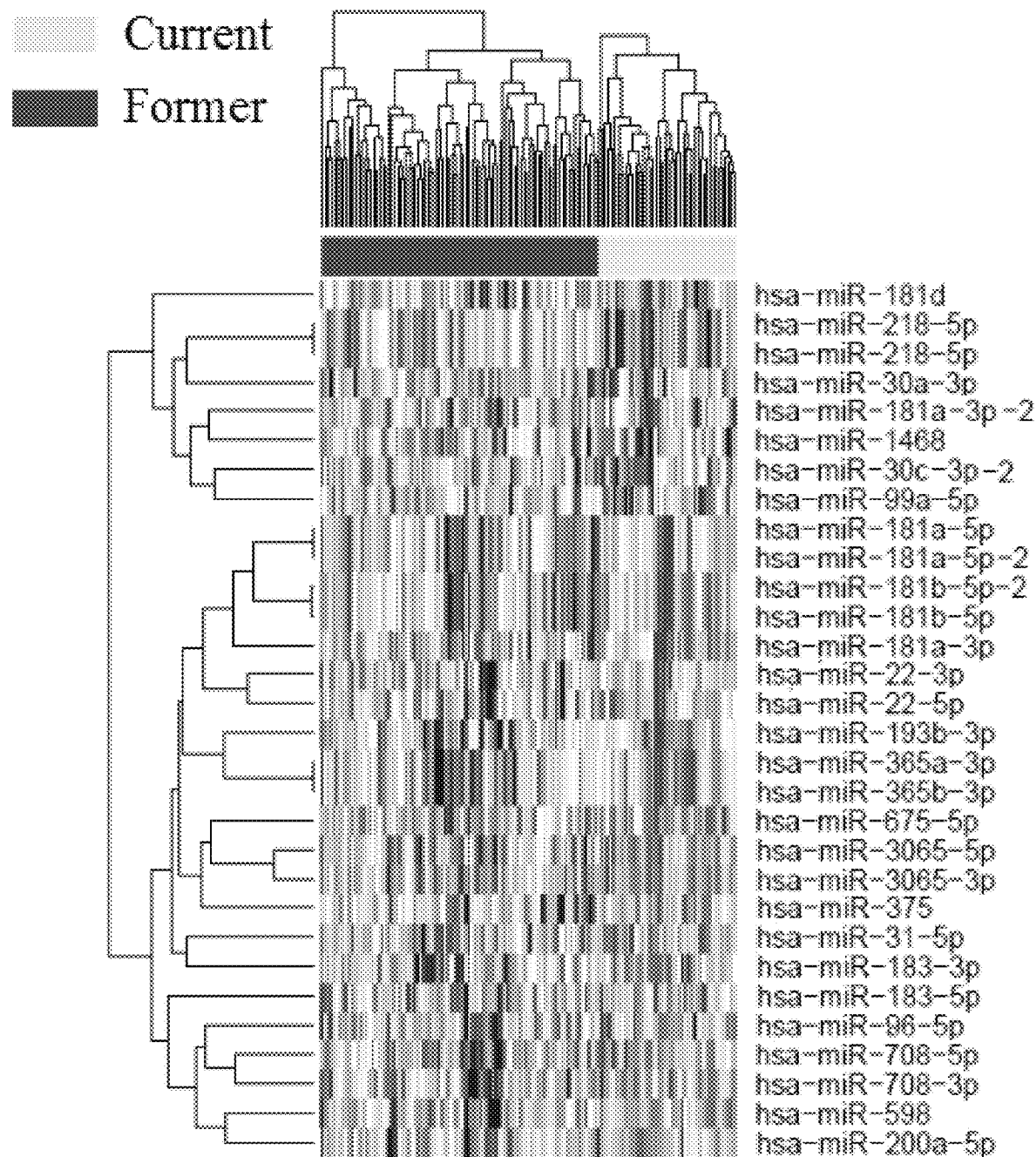

As described herein, the inventors have discovered that the level of certain miRNAs is decreased in lung cancer as opposed to healthy lung tissue. Accordingly, the level of these miRNAs can be used to diagnosis, detect, and/or to treat lung cancer. Additionally, reversing the decrease in the level of the miRNAs can be used to treat lung cancer.

In one aspect of any of the embodiments, described herein is a method comprising detecting the level of expression of at least 1 miRNA selected from the group consisting of: miR-146a-5p, miR-324-5p, miR-223-3p, miR-223-5p; miR-450b-5p, miR-221-3p-miR-505-3p, and miR-582-5p in a sample obtained from a subject. In one aspect of any of the embodiments, described herein is an assay for detecting lung cancer a subject, the assay comprising: subjecting a test sample obtained from a subject to at least one analysis to determine the level of expression of at least 1 miRNAs selected from the group consisting of: miR-146a-5p, miR-324-5p, miR-223-3p, miR-223-5p; miR-450b-5p, miR-221-3p-miR-505-3p, and miR-582-5p; wherein an expression level of the at least 1 miRNA which decreased relative to a reference level, indicates the presence of lung cancer.

In some embodiments of any of the aspects, the methods and assays described herein relate to detecting the level of expression of at least two miRNAs, at least three miRNAs, at least four miRNAs, at least five miRNAs, at least six miRNAs, at least seven miRNAs, or all of the miRNAs of the group consisting of miR-146a-5p, miR-324-5p, miR-223-3p, miR-223-5p; miR-450b-5p, miR-221-3p-miR-505-3p, and miR-582-5p. Where a subset of the 8 foregoing miRNAs is used, any combination of the miRNAs can be used in each of various embodiments of the aspects described herein. For example, when the level of at least two miRNAs is detected, it is specifically contemplated herein that any pairwise combination of the ten miRNAs can be detected, e.g., any combination shown in Table 1.

TABLE 1

Contemplated exemplary combinations of miRNAs are indicated by "X"

| | miR-146a-5p | miR-324-5p | miR-223-3p | miR-223-5p | miR-450b-5p | miR-221-3p | miR-505-3p | miR-582-5p |
|---|---|---|---|---|---|---|---|---|
| miR-146a-5p | | X | X | X | X | X | X | X |
| miR-324-5p | X | | X | X | X | X | X | X |

TABLE 1-continued

Contemplated exemplary combinations of miRNAs are indicated by "X"

| | miR-146a-5p | miR-324-5p | miR-223-3p | miR-223-5p | miR-450b-5p | miR-221-3p | miR-505-3p | miR-582-5p |
|---|---|---|---|---|---|---|---|---|
| miR-223-3p | X | X | | X | X | X | X | X |
| miR-223-5p | X | X | X | | X | X | X | X |
| miR-450b-5p | X | X | X | X | | X | X | X |
| miR-221-3p | X | X | X | X | X | | X | X |
| miR-505-3p | X | X | X | X | X | X | | X |
| miR-582-5p | X | X | X | X | X | X | X | |

In some embodiments of any of the aspects, the levels of expression is detected for at least miR-146-5p, e.g., for miR-146-5p or miR-146-5p and at least one of the other miRNAs described herein. In some embodiments of any of the aspects, the levels of expression is detected for at least miR-146-5p, miR-146a-5p, miR-324-5p, miR-223-3p, and miR-223-5p, e.g., for those four miRNAs or those four miRNAs and at least one of the further miRNAs described herein.

As used herein, "miR-146a-5p" refers to a mature miRNA derived from miR-146a. The sequences for the precursor and mature form are known for a variety of species, e.g. human miR-146a (NCBI Gene ID NO: 406938; NCBI transcript accession number NR_029701.1; SEQ ID NO: 1) and human miR-146a-5p (SEQ ID NO: 2). A "miR-146a-5p oligonucleotide" can be a miR-146a-5p (e.g., SEQ ID NO: 2) or a sequence encoding such an oligonucleotide, e.g. SEQ ID NO: 1. In some embodiments, miR-146a-5p can be human miR-146a-5p, e.g., hsa-miR-146a-5p.

As used herein, "miR-324-5p" refers to a mature miRNA derived from miR-324. The sequences for the precursor and mature form are known for a variety of species, e.g. human miR-324 (NCBI Gene ID NO: 442898; NCBI transcript accession number NR_029896.1; SEQ ID NO: 3) and human miR-324-5p (SEQ ID NO: 4). A "miR-324-5p oligonucleotide" can be a miR-324-5p (e.g., SEQ ID NO: 4) or a sequence encoding such an oligonucleotide, e.g. SEQ ID NO: 3. In some embodiments, miR-324-5p can be human miR-324-5p, e.g., hsa-miR-324-5p.

As used herein, "miR-223-3p" refers to a mature miRNA derived from miR-223. The sequences for the precursor and mature form are known for a variety of species, e.g. human miR-223 (NCBI Gene ID NO: 407008; NCBI transcript accession number NR_029637.1; SEQ ID NO: 5) and human miR-223-3p (SEQ ID NO: 6). A "miR-223-3p oligonucleotide" can be a miR-223-3p (e.g., SEQ ID NO: 6) or a sequence encoding such an oligonucleotide, e.g. SEQ ID NO: 5. In some embodiments, miR-223-3p can be human miR-223-3p, e.g., hsa-miR-223-3p.

As used herein, "miR-223-5p" refers to a mature miRNA derived from miR-223. The sequences for the precursor and mature form are known for a variety of species, e.g. human miR-223 (NCBI Gene ID NO: 407008; NCBI transcript accession number NR_029637.1; SEQ ID NO: 5) and human miR-223-5p (SEQ ID NO: 7). A "miR-223-5p oligonucleotide" can be a miR-223-5p (e.g., SEQ ID NO: 7) or a sequence encoding such an oligonucleotide, e.g. SEQ ID NO: 5. In some embodiments, miR-223-5p can be human miR-223-5p, e.g., hsa-miR-223-5p.

As used herein, "miR-450b-5p" refers to a mature miRNA derived from miR-450b. The sequences for the precursor and mature form are known for a variety of species, e.g. human miR-450b (NCBI Gene ID NO: 100126302; NCBI transcript accession number NR_030587.1; SEQ ID NO: 8) and human miR-450b-5p (SEQ ID NO: 9). A "miR-450b-5p oligonucleotide" can be a miR-450b-5p (e.g., SEQ ID NO: 9) or a sequence encoding such an oligonucleotide, e.g. SEQ ID NO: 8. In some embodiments, miR-450b-5p can be human miR-450b-5p, e.g., hsa-miR-450b-5p.

As used herein, "miR-221-3p" refers to a mature miRNA derived from miR-221. The sequences for the precursor and mature form are known for a variety of species, e.g. human miR-221 (NCBI Gene ID NO: 407006; NCBI transcript accession number NR_029635.1; SEQ ID NO: 10) and human miR-221-3p (SEQ ID NO: 11). A "miR-221-3p oligonucleotide" can be a miR-221-3p (e.g., SEQ ID NO: 11) or a sequence encoding such an oligonucleotide, e.g. SEQ ID NO: 10. In some embodiments, miR-221-3p can be human miR-221-3p, e.g., hsa-miR-221-3p.

As used herein, "miR-505-3p" refers to a mature miRNA derived from miR-505. The sequences for the precursor and mature form are known for a variety of species, e.g. human miR-505 (NCBI Gene ID NO: 574508; NCBI transcript accession number NR_030230.1; SEQ ID NO: 12) and human miR-505-3p (SEQ ID NO: 13). A "miR-505-3p oligonucleotide" can be a miR-505-3p (e.g., SEQ ID NO: 13) or a sequence encoding such an oligonucleotide, e.g. SEQ ID NO: 12. In some embodiments, miR-505-3p can be human miR-505-3p, e.g., hsa-miR-505-3p.

As used herein, "miR-582-5p" refers to a mature miRNA derived from miR-582. The sequences for the precursor and mature form are known for a variety of species, e.g. human miR-582 (NCBI Gene ID NO: 693167; NCBI transcript accession number NR_030308.1; SEQ ID NO: 14) and human miR-582-5p (SEQ ID NO: 15). A "miR-582-5p oligonucleotide" can be a miR-582-5p (e.g., SEQ ID NO: 15) or a sequence encoding such an oligonucleotide, e.g. SEQ ID NO: 14. In some embodiments, miR-582-5p can be human miR-582-5p, e.g., hsa-miR-582-5p.

In one aspect of any of the embodiments, described herein is a method comprising detecting the level of expression of at least 1 miRNA selected from Table 10 and/or at least 1 miRNA selected from Table 11 in a sample obtained from a subject. In one aspect of any of the embodiments, described herein is an assay for detecting lung cancer a subject, the assay comprising: subjecting a test sample obtained from a subject to at least one analysis to determine the level of expression of at least 1 miRNA selected from Table 10 and/or at least 1 miRNA selected from Table 11 wherein an expression level of the at least 1 miRNA from Table 10 which is decreased relative to a reference level, and/or an expression level of the at least 1 miRNA from Table 11 which is increased relative to a reference level, indicates the presence of lung cancer.

In some embodiments of any of the aspects, the methods and assays described herein relate to detecting the level of expression of at least two miRNAs, at least three miRNAs, at least four miRNAs, at least five miRNAs, at least six miRNAs, at least seven miRNAs, or more miRNAs of Tables 10 and/or 11. In some embodiments of any of the aspects, the methods and assays described herein relate to detecting the level of expression of at least one of the miRNAs of the group consisting of miR-146a-5p, miR-324-

5p, miR-223-3p, miR-223-5p; miR-450b-5p, miR-221-3p-miR-505-3p, and miR-582-5p and at least one further miRNA selected from Tables 10 and/or 11. Any combination of the miRNAs can be used in each of various embodiments of the aspects described herein.

TABLE 10 miRNAs downregulated in lung cancer
microRNA name miR-324-5p
miR-223-3p
miR-146a-5p
miR-223-5p
miR-769-3p
miR-618
miR-338-5p
miR-210
miR-450a-5p
miR-30b-5p
miR-450a-5p
miR-34a-5p
miR-652-3p
miR-107
miR-887
miR-147b
miR-31-5p
miR-29c-5p
miR-324-3p
miR-345-5p
miR-450b-5p
miR-769-5p
miR-326
miR-940
let-7g-5p
miR-582-5p
miR-31-3p
miR-378i
miR-505-3p
miR-1249
miR-221-3p
miR-1260b
miR-3200-3p
miR-425-3p
miR-4791
miR-1296
miR-4677-3p

TABLE 11 miRNAs upregulated in lung cancer
microRNA name miR-375
miR-24-1-5p
miR-130b-5p
miR-183-5p
miR-203a In some embodiments of any of the aspects, the detecting step can comprise sequencing miRNAs present in the sample. In some embodiments of any of the aspects, the detecting step can comprise hybridization of miRNAs in the sample with probes, e.g., miRNA-specific probes.

In some embodiments, measurement of the level of a target and/or detection of the level or presence of a target, e.g. of an expression product (a RNA expression product of one of the genes described herein) can comprise a transformation. As used herein, the term "transforming" or "transformation" refers to changing an object or a substance, e.g., biological sample, nucleic acid or protein, into another substance. The transformation can be physical, biological or chemical. Exemplary physical transformation includes, but is not limited to, pre-treatment of a biological sample, e.g., from whole blood to blood serum by differential centrifugation. A biological/chemical transformation can involve the action of at least one enzyme and/or a chemical reagent in a reaction. For example, a DNA sample can be digested into fragments by one or more restriction enzymes, or an exogenous molecule can be attached to a fragmented DNA sample with a ligase. In some embodiments, a nucleic acid sample can undergo enzymatic replication, e.g., by polymerase chain reaction (PCR).

Transformation, measurement, and/or detection of a target molecule, e.g. a miRNA and/or mRNA as described herein can comprise contacting a sample obtained from a subject with a reagent (e.g. a detection reagent) which is specific for the target, e.g., a target-specific reagent. In some embodiments, the target-specific reagent is detectably labeled. In some embodiments, the target-specific reagent is capable of generating a detectable signal. In some embodiments, the target-specific reagent generates a detectable signal when the target molecule is present. In some embodiments of any of the aspects, the target-specific reagent hybridizes to the target, e.g., through base pairing interactions.

Methods to measure gene expression products are known to a skilled artisan. In some embodiments, the methods described herein can relate to determining the level of messenger RNA (mRNA) or miRNA described herein. Such molecules can be isolated, derived, or amplified from a biological sample, such as a bronchial brushing sample. Techniques for the detection of mRNA and/or miRNA expression is known by persons skilled in the art, and can include but not limited to, PCR procedures, RT-PCR, quantitative RT-PCR Northern blot analysis, differential gene expression, RNAse protection assay, microarray based analysis, next-generation sequencing; hybridization methods, etc.

In some embodiments, the level of an miRNA and/or mRNA can be measured by a quantitative sequencing technology, e.g. a quantitative next-generation sequence technology. Methods of sequencing a nucleic acid sequence are well known in the art. Briefly, a sample obtained from a subject can be contacted with one or more primers which specifically hybridize to a single-strand nucleic acid sequence flanking the target gene sequence and a complementary strand is synthesized. In some next-generation technologies, an adaptor (double or single-stranded) is ligated to nucleic acid molecules in the sample and synthesis proceeds from the adaptor or adaptor compatible primers. In some third-generation technologies, the sequence can be determined, e.g. by determining the location and pattern of the hybridization of probes, or measuring one or more characteristics of a single molecule as it passes through a sensor (e.g. the modulation of an electrical field as a nucleic acid molecule passes through a nanopore). Exemplary methods of sequencing include, but are not limited to, Sanger sequencing, dideoxy chain termination, high-throughput sequencing, next generation sequencing, 454 sequencing, SOLiD sequencing, polony sequencing, Illumina sequencing, Ion Torrent sequencing, sequencing by hybridization, nanopore sequencing, Helioscope sequencing, single molecule real time sequencing, RNAP sequencing, and the like. Methods and protocols for performing these sequencing methods are known in the art, see, e.g. "Next Generation Genome Sequencing" Ed. Michal Janitz, Wiley-VCH; "High-Throughput Next Generation Sequencing" Eds. Kwon and Ricke, Humanna Press, 2011; and Sambrook et al., Molecular Cloning: A Laboratory Manual (4 ed.), Cold Spring Harbor Laboratory Press, Cold Spring Harbor, N.Y., USA (2012); which are incorporated by reference herein in their entireties.

The nucleic acid sequences of the miRNAs described herein have been assigned miR BASE and NCBI accession numbers for different species such as human, mouse and rat. Accordingly, a skilled artisan can design an appropriate primer or hybridization probe based on the known sequence for determining the expression level of the indicated molecule.

In some embodiments of any of the aspects, the methods and assays described herein can further comprise detecting the expression level of one or more mRNAs.

In some embodiments of any of the aspects, the methods and assays described herein comprise detecting the expression level of no more than 100 miRNAs and/or mRNAs. In some embodiments of any of the aspects, the methods and assays described herein comprise detecting the expression level of no more than 20 miRNAs and/or mRNAs. In some embodiments of any of the aspects, the methods and assays described herein comprise detecting the expression level of no more than 50 miRNAs and/or mRNAs.

Nucleic acid and ribonucleic acid (RNA) molecules can be isolated from a particular biological sample using any of a number of procedures, which are well-known in the art, the particular isolation procedure chosen being appropriate for the particular biological sample. For example, freeze-thaw and alkaline lysis procedures can be useful for obtaining nucleic acid molecules from solid materials; heat and alkaline lysis procedures can be useful for obtaining nucleic acid molecules from urine; and proteinase K extraction can be used to obtain nucleic acid from blood (Roiff, A et al. PCR: Clinical Diagnostics and Research, Springer (1994)).

The term "sample" or "test sample" as used herein denotes a sample taken or isolated from a biological organism, e.g., a bronchial brushing, epithiel cell, blood, or plasma sample from a subject. Exemplary biological samples include, but are not limited to, a biopsy, a tumor sample, biofluid sample; serum; plasma; urine; saliva; and/or tissue sample etc. The term also includes a mixture of the above-mentioned samples. The term "test sample" also includes untreated or pretreated (or pre-processed) biological samples. In some embodiments, a test sample can comprise cells from a subject. In some embodiments, the test sample can be a biopsy, tumor sample, or lung or respiratory sample.

In some embodiments, the test sample can be an untreated test sample. As used herein, the phrase "untreated test sample" refers to a test sample that has not had any prior sample pre-treatment except for dilution and/or suspension in a solution. Exemplary methods for treating a test sample include, but are not limited to, centrifugation, filtration, sonication, homogenization, heating, freezing and thawing, and combinations thereof. In some embodiments, the test sample can be a frozen test sample, e.g., a frozen tissue. The frozen sample can be thawed before employing methods, assays and systems described herein. After thawing, a frozen sample can be centrifuged before being subjected to methods, assays and systems described herein. In some embodiments, the test sample is a clarified test sample, for example, prepared by centrifugation and collection of a supernatant comprising the clarified test sample. In some embodiments, a test sample can be a pre-processed test sample, for example, supernatant or filtrate resulting from a treatment selected from the group consisting of centrifugation, filtration, thawing, purification, and any combinations thereof. In some embodiments, the test sample can be treated with a chemical and/or biological reagent. Chemical and/or biological reagents can be employed to protect and/or maintain the stability of the sample, including biomolecules (e.g., nucleic acid and protein) therein, during processing. The skilled artisan is well aware of methods and processes appropriate for pre-processing of biological samples required for determination of the level miRNAs as described herein.

In some embodiments of any of the aspects, the sample is a sample of epithelial cells from the respiratory tract. In some embodiments of any of the aspects, the sample is a bronchial brushing or nasal epithelial sample. In some embodiments of any of the aspects, the sample is an aspirate sample.

The test sample can be obtained by removing a sample from a subject, but can also be accomplished by using a previously isolated sample (e.g. isolated at a prior timepoint and isolated by the same or another person). In some embodiments of any of the aspects, the methods and assays described herein can further comprise a step of obtaining a sample from a subject.

In some embodiments of any of the aspects, the subject is a mammal. In some embodiments of any of the aspects, the subject is a primate. In some embodiments of any of the aspects, the subject is a human.

A level which is less than a reference level can be a level which is less by at least about 10%, at least about 20%, at least about 50%, at least about 60%, at least about 80%, at least about 90%, or less than the reference level. In some embodiments, a level which is less than a reference level can be a level which is statistically significantly less than the reference level.

A level which is greater than a reference level can be a level which is greater by at least about 10%, at least about 20%, at least about 50%, at least about 100%, at least about 200%, at least about 300% or more than the reference level. A level which is greater than a reference level can be a level which is greater by at least about 1 $\sigma$ on a statistical comparison with normal subjects, preferentially at least 2 $\sigma$. In some embodiments, a level which is greater than a reference level can be a level which is statistically significantly greater than the reference level.

In some embodiments, the reference can be a level of the target molecule in a population of subjects who do not have or are not diagnosed as having, and/or do not exhibit signs or symptoms of a cancer (e.g., lung cancer). In some embodiments, the reference can also be a level of expression of the target molecule in a control sample, a pooled sample of control individuals or a numeric value or range of values based on the same. In some embodiments, the reference can be the level of a target molecule in a sample obtained from the same subject at an earlier point in time, e.g., the methods described herein can be used to determine if a subject's sensitivity to a given therapy is changing over time or if the subject is at greater risk of having or developing lung cancer as compared to in the past.

In some embodiments of any of the aspects, the subject is a current or former cigarette smoker. In some embodiments of any of the aspects, the subject is a subject at risk of developing lung cancer, e.g., a subject with a family history of lung cancer, a subject who is a current or former cigarette smoker, a subject exposed to one or more risk factors for lung cancer, and/or a subject displaying one or more symptoms of or associated with lung cancer.

In some embodiments of any of the aspects described herein, the methods or assays can comprise a further step of administering a treatment for lung cancer to the subject, e.g., if the expression level of at least one miRNA described herein (e.g., one of the miRNAs of Table 1 or 10) is determined to be decreased relative to a reference level. In some embodiments of any of the aspects described herein, the methods or assays can comprise a further step of administering a treatment for lung cancer to the subject, e.g., if the expression level of at least one miRNA of Table 11 is determined to be increased relative to a reference level. In one aspect of any of the embodiments, described herein is a method of treating lung cancer in a subject in need thereof, the method comprising subjecting a test sample obtained from a subject to at least one analysis to determine the level of expression of at least 1 miRNAs selected from the group consisting of: miR-146a-5p, miR-324-5p, miR-223-3p, miR-223-5p; miR-450b-5p, miR-221-3p-miR-505-3p, and miR-582-5p; and administering a treatment for lung cancer to the subject if the expression level of the at least 1 miRNA is decreased relative to a reference level. In one aspect of any of the embodiments, described herein is a method of treating lung cancer in a subject in need thereof, the method comprising subjecting a test sample obtained from a subject to at least one analysis to determine the level of expression of at least 1 miRNAs selected from the group consisting of: miR-146a-5p, miR-324-5p, miR-223-3p, miR-223-5p; miR-450b-5p, miR-221-3p-miR-505-3p, and miR-582-5p; and administering a treatment for lung cancer to the subject when the expression level of the at least 1 miRNA is decreased relative to a reference level.

In one aspect of any of the embodiments, described herein is a method of treating lung cancer in a subject in need thereof, the method comprising subjecting a test sample obtained from a subject to at least one analysis to determine the level of expression of at least 1 miRNAs from Table 10 and/or at least one miRNA from Table 11; and administering a treatment for lung cancer to the subject if the expression level of the at least 1 miRNA from Table 10 is decreased relative to a reference level and/or if the at least one miRNA from Table 11 is increased relative to a reference level. In one aspect of any of the embodiments, described herein is a method of treating lung cancer in a subject in need thereof, the method comprising subjecting a test sample obtained from a subject to at least one analysis to determine the level of expression of at least 1 miRNAs selected from Table 10 and/or at least one miRNA selected from Table 11; and administering a treatment for lung cancer to the subject when the expression level of the at least 1 miRNA of Table 10 is decreased relative to a reference level and/or when the expression level of the at least 1 miRNA of Table 11 is decreased relative to a reference level.

In one aspect of any of the embodiments, described herein is a method of treating lung cancer in a subject in need thereof, the method comprising administering a treatment for lung cancer to a subject determined to have an expression level of at least 1 miRNA selected from the group consisting of: miR-146a-5p, miR-324-5p, miR-223-3p, miR-223-5p; miR-450b-5p, miR-221-3p-miR-505-3p, and miR-582-5p in a sample obtained from the subject which is decreased relative to a reference level. In one aspect of any of the embodiments, described herein is a method of treating lung cancer in a subject in need thereof, the method comprising administering a treatment for lung cancer to a subject determined to have an expression level of at least 1 miRNA selected from Table 10 in a sample obtained from the subject which is decreased relative to a reference level and/or an expression level of at least 1 miRNA selected from Table 11 in a sample obtained from the subject which is increased relative to a reference level.

In some embodiments of any of the aspects, a treatment for lung cancer can comprise an agonist of at least 1 miRNAs selected from the group consisting of: miR-146a-5p, miR-324-5p, miR-223-3p, miR-223-5p; miR-450b-5p, miR-221-3p-miR-505-3p, and miR-582-5p. In some embodiments of any of the aspects, a treatment for lung cancer can comprise an agonist of at least 1 miRNA selected from Table 10. In some embodiments of any of the aspects, a treatment for lung cancer can comprise an inhibitor of at least 1 miRNA selected from Table 11.

As used herein, an "agonist" of the expression of an miRNA, e.g., refers to any agent that increases the expression and/or level of the miRNA, e.g. increases the expression of the miRNA by at least 10%, at least 20%, at least 30%, at least 50%, at least 100%, at least 200%, at least 500% or more. In some embodiments, the agonist can be a miRNA oligonucleotide and/or a vector encoding a miRNA oligonucleotide. In some embodiments of any of the aspects, an agonist of an miRNA can be the sequence of a naturally-occurring variant of the miRNA or the gene encoding the miRNA, e.g., a sequence of the miRNA as known in miRBase or the NCBI database for human or other species. In some embodiments of any of the aspects, an agonist of a miRNA can be a miRNA selected from the group consisting of miR-146a-5p, miR-324-5p, miR-223-3p, miR-223-5p; miR-450b-5p, miR-221-3p-miR-505-3p, and miR-582-5p or a nucleic acid encoding one of the foregoing miRNAs.

In some embodiments of any of the aspects, an agonist of a miRNA can be a miRNA or a nucleic acid encoding an miR that has at least 90%, at least 92%, at least 95%, at least 98%, or at least 99% sequence identity with the target miRNA. In some embodiments of any of the aspects, an agonist of an miRNA can be a miRNA or a nucleic acid encoding an miR that has at least 90%, at least 92%, at least 95%, at least 98%, or at least 99% sequence identity with the target miRNA and shares the activity of the wild-type and/or naturally-occurring miRNA.

As used herein, the term "inhibitor" refers to an agent which can decrease the expression of an miRNA, e.g. by at least 10% or more, e.g. by 10% or more, 50% or more, 70% or more, 80% or more, 90% or more, 95% or more, or 98% or more. The efficacy of an inhibitor of one or more targets, e.g. its ability to decrease the level target miRNA can be determined, e.g. by measuring the level of an expression product of the target and/or the activity of the target. Methods for measuring the level of a given mRNA are known to one of skill in the art, e.g. RT-PCR with primers can be used to determine the level of RNA. In some embodiments, the inhibitor can be an inhibitory nucleic acid; an aptamer; an antibody reagent; an antibody; or a small molecule. In some embodiments, the inhibitor can be an inhibitory nucleic acid.

Inhibitors of the expression of a given miRNA can be an inhibitory nucleic acid. In some embodiments, the inhibitory nucleic acid is an inhibitory RNA (iRNA). Double-stranded RNA molecules (dsRNA) have been shown to block gene expression in a highly conserved regulatory mechanism known as RNA interference (RNAi). The inhibitory nucleic acids described herein can include an RNA strand (the antisense strand) having a region which is 30 nucleotides or less in length, i.e., 15-30 nucleotides in length, generally 19-24 nucleotides in length, which region is substantially complementary to at least part the targeted mRNA transcript. The use of these iRNAs enables the targeted degradation of targeted mRNAs, resulting in decreased expression and/or activity of the target.

As used herein, the term "iRNA" refers to an agent that contains RNA as that term is defined herein, and which mediates the targeted cleavage of an RNA transcript via an RNA-induced silencing complex (RISC) pathway. In one embodiment, an iRNA as described herein effects inhibition of the expression and/or activity of a target. In certain embodiments, contacting a cell with the inhibitor (e.g. an iRNA) results in a decrease in the target RNA level in a cell by at least about 5%, about 10%, about 20%, about 30%, about 40%, about 50%, about 60%, about 70%, about 80%, about 90%, about 95%, about 99%, up to and including 100% of the target mRNA level found in the cell without the presence of the iRNA.

In some embodiments, the iRNA can be a dsRNA. A dsRNA includes two RNA strands that are sufficiently complementary to hybridize to form a duplex structure under conditions in which the dsRNA will be used. One strand of a dsRNA (the antisense strand) includes a region of complementarity that is substantially complementary, and generally fully complementary, to a target sequence. The target sequence can be derived from the sequence of an mRNA formed during the expression of the target. The other strand (the sense strand) includes a region that is complementary to the antisense strand, such that the two strands hybridize and form a duplex structure when combined under suitable conditions. Generally, the duplex structure is between 15 and 30 inclusive, more generally between 18 and 25 inclusive, yet more generally between 19 and 24 inclusive, and most generally between 19 and 21 base pairs in length, inclusive. Similarly, the region of complementarity to the target sequence is between 15 and 30 inclusive, more generally between 18 and 25 inclusive, yet more generally between 19 and 24 inclusive, and most generally between 19 and 21 nucleotides in length, inclusive. In some embodiments, the dsRNA is between 15 and 20 nucleotides in length, inclusive, and in other embodiments, the dsRNA is between 25 and 30 nucleotides in length, inclusive. As the ordinarily skilled person will recognize, the targeted region of an RNA targeted for cleavage will most often be part of a larger RNA molecule, often an mRNA molecule. Where relevant, a "part" of an mRNA target is a contiguous sequence of an mRNA target of sufficient length to be a substrate for RNAi-directed cleavage (i.e., cleavage through a RISC pathway). dsRNAs having duplexes as short as 9 base pairs can, under some circumstances, mediate RNAi-directed RNA cleavage. Most often a target will be at least 15 nucleotides in length, preferably 15-30 nucleotides in length.

In some embodiments of any of the aspects, the subject is contacted with and/or administered at least one nucleic acid encoding exogenous and/or ectopic miRNA and/or inhibitory nucleic acids, e.g., the nucleic acid is transcribed after the administering step to provide exogenous and/or ectopic miRNA and/or inhibitory nucleic acids to the subject.

In one aspect of any of the embodiments, described herein is a method of treating lung cancer in a subject in need thereof, the method comprising administering to the subject an agonist of at least 1 miRNA selected from the group consisting of: miR-146a-5p, miR-324-5p, miR-223-3p; miR-223-5p; miR-450b-5p, miR-221-3p-miR-505-3p, and miR-582-5p. In one aspect of any of the embodiments, described herein is a method of treating lung cancer in a subject in need thereof, the method comprising administering to the subject an agonist of at least 1 miRNA selected from Table 10 and/or at an inhibitor of at least 1 miRNA selected from Table 11.

In one aspect of any of the embodiments, described herein is is a pharmaceutical composition comprising an agonist of at least 1 miRNA selected from the group consisting of miR-146a-5p, miR-324-5p, miR-223-3p, miR-223-5p; miR-450b-5p, miR-221-3p-miR-505-3p, and miR-582-5p. In one aspect of any of the embodiments, described herein is is a pharmaceutical composition comprising an agonist of at least 1 miRNA selected from Table 10 and/or an inhibitor of at least 1 miRNA selected from Table 11. As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In some embodiments of any of the aspects, a pharmaceutically acceptable carrier can be a carrier other than water. In some embodiments of any of the aspects, a pharmaceutically acceptable carrier can be a cream, emulsion, gel, liposome, nanoparticle, and/or ointment. In some embodiments of any of the aspects, a pharmaceutically acceptable carrier can be an artificial or engineered carrier, e.g., a carrier that the active ingredient would not be found to occur in in nature.

In some embodiments, the methods described herein relate to treating a subject having or diagnosed as having lung cancer (e.g., small cell lung cancer or non-small cell lung cancer. Subjects having lung cancer can be identified by a physician using current methods of diagnosing lung cancer. Symptoms and/or complications of lung cancer which characterize these conditions and aid in diagnosis are well known in the art and include but are not limited to, coughing, coughing blood, shortness of breath, chest pain, wheezing, hoarseness, difficulty breathing, unexplained weight loss, bone pain, and headaches. Tests that may aid in a diagnosis of, e.g. lung cancer include, but are not limited to, x-rays, CT scan, sputum cytology, or biopsies. A family history of lung cancer, or exposure to risk factors for lung cancer (e.g. radon or asbestos exposure) can also aid in determining if a subject is likely to have lung cancer or in making a diagnosis of lung cancer.

As used herein, the term "cancer" relates generally to a class of diseases or conditions in which abnormal cells divide without control and can invade nearby tissues. Cancer cells can also spread to other parts of the body through the blood and lymph systems. There are several main types of cancer. Carcinoma is a cancer that begins in the skin or in tissues that line or cover internal organs. Sarcoma is a cancer that begins in bone, cartilage, fat, muscle, blood vessels, or other connective or supportive tissue. Leukemia is a cancer that starts in blood-forming tissue such as the bone marrow, and causes large numbers of abnormal blood cells to be produced and enter the blood. Lymphoma and multiple myeloma are cancers that begin in the cells of the immune system. Central nervous system cancers are cancers that begin in the tissues of the brain and spinal cord.

In some embodiments of any of the aspects, the cancer is a primary cancer. In some embodiments of any of the aspects, the cancer is a malignant cancer. As used herein, the term "malignant" refers to a cancer in which a group of tumor cells display one or more of uncontrolled growth (i.e., division beyond normal limits), invasion (i.e., intrusion on and destruction of adjacent tissues), and metastasis (i.e., spread to other locations in the body via lymph or blood). As used herein, the term "metastasize" refers to the spread of cancer from one part of the body to another. A tumor formed by cells that have spread is called a "metastatic tumor" or a "metastasis." The metastatic tumor contains cells that are like those in the original (primary) tumor. As used herein, the term "benign" or "non-malignant" refers to tumors that may grow larger but do not spread to other parts of the body. Benign tumors are self-limited and typically do not invade or metastasize.

A "cancer cell" or "tumor cell" refers to an individual cell of a cancerous growth or tissue. A tumor refers generally to a swelling or lesion formed by an abnormal growth of cells, which may be benign, pre-malignant, or malignant. Most cancer cells form tumors, but some, e.g., leukemia, do not necessarily form tumors. For those cancer cells that form tumors, the terms cancer (cell) and tumor (cell) are used interchangeably.

A subject that has a cancer or a tumor is a subject having objectively measurable cancer cells present in the subject's body. Included in this definition are malignant, actively proliferative cancers, as well as potentially dormant tumors or micrometastatses. Cancers which migrate from their original location and seed other vital organs can eventually lead to the death of the subject through the functional deterioration of the affected organs.

Treatments for lung cancer can include radiation therapy, stereotactic body radiotherapy, surgery (e.g. resection, lobesctomy, or pneumonectomy), chemotherapy, treatment with afatinib, bevacizumab, certinib, crizotinib, erlotinib, nivoluman, or ramucirumab.

In some embodiments, the methods described herein comprise administering an effective amount of a composition described herein, e.g. an agonist of an miRNA described herein to a subject in order to alleviate a symptom of a lung cancer. As used herein, "alleviating a symptom" is ameliorating any condition or symptom associated with the disease. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to oral, parenteral, intravenous, intramuscular, subcutaneous, transdermal, airway (aerosol), pulmonary, cutaneous, topical, injection, or intratumoral administration. Administration can be local or systemic.

The term "effective amount" as used herein refers to the amount of an agent needed to alleviate at least one or more symptom of the disease or disorder, and relates to a sufficient amount of pharmacological composition to provide the desired effect. The term "therapeutically effective amount" therefore refers to an amount of the agent that is sufficient to provide a particular effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of the agent, which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for tumor growth and/or size, among others. The dosage can be determined by a physician and adjusted, as necessary, to suit observed effects of the treatment.

In some embodiments, the agonist or inhibitor of a miRNA can be provided or administered on a vector, e.g., a viral vector. In some embodiments, the agonist or inhibitor of a miRNA can be provided or administered as a gene therapy.

In some embodiments, the technology described herein relates to a pharmaceutical composition comprising an agonist or inhibitor of a miRNA as described herein, and optionally a pharmaceutically acceptable carrier. In some embodiments, the active ingredients of the pharmaceutical composition comprise an agonist or an inhibitor of a miRNA as described herein. In some embodiments, the active ingredients of the pharmaceutical composition consist essentially of an agonist or an inhibitor of a miRNA as described herein. In some embodiments, the active ingredients of the pharmaceutical composition consist of an agonist or an inhibitor of a miRNA as described herein. Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of the active agent.

In some embodiments, the pharmaceutical composition as described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, DUROS®-type dosage forms and dose-dumping.

Suitable vehicles that can be used to provide parenteral dosage forms are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt of an agonist and/or inhibitor of a miRNA as disclosed herein can also be incorporated into the parenteral dosage forms of the disclosure, including conventional and controlled-release parenteral dosage forms.

Pharmaceutical compositions can also be formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington: The Science and Practice of Pharmacy, 21st Ed., Lippincott, Williams, and Wilkins, Philadelphia Pa. (2005).

In some embodiments of any of the aspects, the compositions described herein can be administered by inhalation, e.g., as a vapor or aerosol formulation or by nebulization. For use as aerosols, a composition described herein can be provided in solution or suspension may be packaged in a pressurized aerosol container together with suitable propellants, for example, hydrocarbon propellants like propane, butane, or isobutane with conventional adjuvants. A composition described herein can also be administered in a non-pressurized form such as in a nebulizer or atomizer. In some embodiments, a composition can also be administered directly to the airways in the form of a dry powder, e.g., by use with an inhaler. Aerosols for the delivery to the respiratory tract are known in the art. See for example, Adjei, A. and Garren, J. Pharm. Res., 1: 565-569 (1990); Zanen, P. and Lamm, J.-W. J. Int. J. Pharm., 114: 111-115 (1995); Gonda, I. "Aerosols for delivery of therapeutic and diagnostic agents to the respiratory tract," in Critical Reviews in Therapeutic Drug Carrier Systems, 6:273-313 (1990); Anderson et al., Am. Rev. Respir. Dis., 140: 1317-1324 (1989)) and have potential for the systemic delivery of peptides and proteins as well (Patton and Platz, Advanced Drug Delivery Reviews, 8:179-196 (1992)); Timsina et. al., Int. J. Pharm., 101: 1-13 (1995); and Tansey, I. P., Spray Technol. Market, 4:26-29 (1994); French, D. L., Edwards, D. A. and Niven, R. W., Aerosol Sci., 27: 769-783 (1996); Visser, J., Powder Technology 58: 1-10 (1989)); Rudt, S. and R. H. Muller, J. Controlled Release, 22: 263-272 (1992); Tabata, Y, and Y. Ikada, Biomed. Mater. Res., 22: 837-858 (1988); Wall, D. A., Drug Delivery, 2: 10 1-20 1995); Patton, J. and Platz, R., Adv. Drug Del. Rev., 8: 179-196 (1992); Bryon, P., Adv. Drug. Del. Rev., 5: 107-132 (1990); Patton, J. S., et al., Controlled Release, 28: 15 79-85 (1994); Damms, B. and Bains, W., Nature Biotechnology (1996); Niven, R. W., et al., Pharm. Res., 12(9); 1343-1349 (1995); and Kobayashi, S., et al., Pharm. Res., 13(1): 80-83 (1996), contents of all of which are herein incorporated by reference in their entirety.

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments, the an agonist and/or inhibitor of a miRNA described herein can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

In some embodiments of any of the aspects, the an agonist and/or inhibitor of a miRNA described herein is administered as a monotherapy, e.g., another treatment for the lung cancer is not administered to the subject.

In some embodiments of any of the aspects, the methods described herein can further comprise administering a second agent and/or treatment to the subject, e.g. as part of a combinatorial therapy. Non-limiting examples of a second agent and/or treatment can include lung cancer treatments as described elsewhere herein, and/or radiation therapy, surgery, gemcitabine, cisplastin, paclitaxel, carboplatin, bortezomib, AMG479, vorinostat, rituximab, temozolomide, rapamycin, ABT-737, PI-103; alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholphosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1l (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb®); inhibitors of PKC-alpha, Raf, H-Ras, EGFR (e.g., erlotinib (Tarceva®)) and VEGF-A that reduce cell proliferation and pharmaceutically acceptable salts, acids or derivatives of any of the above.

In addition, the methods of treatment can further include the use of radiation or radiation therapy. Further, the methods of treatment can further include the use of surgical treatments.

One of skill in the art can readily identify a chemotherapeutic agent of use (e.g. see Physicians' Cancer Chemotherapy Drug Manual 2014, Edward Chu, Vincent T. DeVita Jr., Jones & Bartlett Learning; Principles of Cancer Therapy, Chapter 85 in Harrison's Principles of Internal Medicine, 18th edition; Therapeutic Targeting of Cancer Cells: Era of Molecularly Targeted Agents and Cancer Pharmacology, Chs. 28-29 in Abeloff's Clinical Oncology, 2013 Elsevier; and Fischer D S (ed): The Cancer Chemotherapy Handbook, 4th ed. St. Louis, Mosby-Year Book, 2003).

In certain embodiments, an effective dose of a composition comprising an agonist and/or inhibitor of a miRNA as described herein can be administered to a patient once. In certain embodiments, an effective dose of a composition can be administered to a patient repeatedly. For systemic administration, subjects can be administered a therapeutic amount of a composition, such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

In some embodiments, after an initial treatment regimen, the treatments can be administered on a less frequent basis. For example, after treatment biweekly for three months, treatment can be repeated once per month, for six months or a year or longer. Treatment according to the methods described herein can reduce levels of a marker or symptom of a condition, e.g. lung cancer by at least 10%, at least 15%, at least 20%, at least 25%, at least 30%, at least 40%, at least 50%, at least 60%, at least 70%, at least 80% or at least 90% or more.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to the active agent. The desired dose or amount of activation can be administered at one time or divided into subdoses, e.g., 2-4 subdoses and administered over a period of time, e.g., at appropriate intervals through the day or other appropriate schedule. In some embodiments, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. A composition can be administered over a period of time, such as over a 5 minute, 10 minute, 15 minute, 20 minute, or 25 minute period.

The dosage ranges for the administration of an agent according to the methods described herein depend upon, for example, the form of the agent, its potency, and the extent to which symptoms, markers, or indicators of a condition described herein are desired to be reduced, for example the percentage reduction desired for tumor growth. The dosage should not be so large as to cause adverse side effects. Generally, the dosage will vary with the age, condition, and sex of the patient and can be determined by one of skill in the art. The dosage can also be adjusted by the individual physician in the event of any complication.

The efficacy of an agent described herein in, e.g. the treatment of a condition described herein, or to induce a response as described herein (e.g. lung cancer) can be determined by the skilled clinician. However, a treatment is considered "effective treatment," as the term is used herein, if one or more of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate, e.g. tumor size and/or growth rate. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g. pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response. It is well within the ability of one skilled in the art to monitor efficacy of administration and/or treatment by measuring any one of such parameters, or any combination of parameters. Efficacy can be assessed in animal models of a condition described herein, for example treatment of lung cancer in a mouse model. When using an experimental animal model, efficacy of treatment is evidenced when a statistically significant change in a marker is observed, e.g. tumor size and/or growth rate.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

The term "exogenous" refers to a substance present in a cell other than its native source. The term "exogenous" when used herein can refer to a nucleic acid (e.g., a miRNA or nucleic acid encoding a miRNA) that has been introduced by a process involving the hand of man into a biological system such as a cell or organism in which it is not normally found and one wishes to introduce the nucleic acid or polypeptide into such a cell or organism. Alternatively, "ectopic" can refer to a nucleic acid that has been introduced by a process involving the hand of man into a biological system such as a cell or organism in which it is found in relatively low amounts and one wishes to increase the amount of the nucleic acid or polypeptide in the cell or organism, e.g., to create ectopic expression or levels. In contrast, the term "endogenous" refers to a substance that is native to the biological system or cell.

As used herein, a "subject" means a human or animal. Usually the animal is a vertebrate such as a primate, rodent, domestic animal or game animal. Primates include chimpanzees, cynomolgous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of, e.g., lung cancer. A subject can be male or female.

A subject can be one who has been previously diagnosed with or identified as suffering from or having a condition in need of treatment (e.g. lung cancer) or one or more complications related to such a condition, and optionally, have already undergone treatment for the condition or the one or more complications related to the condition. Alternatively, a subject can also be one who has not been previously diagnosed as having the condition or one or more complications related to the condition. For example, a subject can be one who exhibits one or more risk factors for the condition or one or more complications related to the condition or a subject who does not exhibit risk factors.

A "subject in need" of treatment for a particular condition can be a subject having that condition, diagnosed as having that condition, or at risk of developing that condition.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable DNA can include, e.g., genomic DNA or cDNA. Suitable RNA can include, e.g., mRNA or miRNA.

In some embodiments of any of the aspects, a nucleic acid as described herein (e.g. a a miRNA or a nucleic acid encoding an miRNA) is comprised by a vector. In some of the aspects described herein, a nucleic acid sequence as described herein, or any module thereof, is operably linked to a vector. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification. The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

As used herein, the term "viral vector" refers to a nucleic acid vector construct that includes at least one element of viral origin and has the capacity to be packaged into a viral vector particle. The viral vector can contain the nucleic acid encoding a polypeptide as described herein in place of non-essential viral genes. The vector and/or particle may be utilized for the purpose of transferring any nucleic acids into cells either in vitro or in vivo. Numerous forms of viral vectors are known in the art.

By "recombinant vector" is meant a vector that includes a heterologous nucleic acid sequence, or "transgene" that is capable of expression in vivo. It should be understood that the vectors described herein can, in some embodiments of any of the aspects, be combined with other suitable compositions and therapies. In some embodiments of any of the aspects, the vector is episomal. The use of a suitable episomal vector provides a means of maintaining the nucleotide of interest in the subject in high copy number extra chromosomal DNA thereby eliminating potential effects of chromosomal integration.

In some embodiments of any of the aspects, an agonist and/or inhibitor of an miRNA as described herein can comprise a modified nucleic acid sequence, e.g., it is chemically modified to enhance stability or other beneficial characteristics. The nucleic acids described herein may be synthesized and/or modified by methods well established in the art, such as those described in "Current protocols in nucleic acid chemistry," Beaucage, S. L. et al. (Edrs.), John Wiley & Sons, Inc., New York, N.Y., USA, which is hereby incorporated herein by reference. Modifications include, for example, (a) end modifications, e.g., 5' end modifications (phosphorylation, conjugation, inverted linkages, etc.) 3' end modifications (conjugation, DNA nucleotides, inverted linkages, etc.), (b) base modifications, e.g., replacement with stabilizing bases, destabilizing bases, or bases that base pair with an expanded repertoire of partners, removal of bases (abasic nucleotides), or conjugated bases, (c) sugar modifications (e.g., at the 2' position or 4' position) or replacement of the sugar, as well as (d) backbone modifications, including modification or replacement of the phosphodiester linkages. Specific examples of RNA compounds useful in the embodiments described herein include, but are not limited to RNAs containing modified backbones or no natural internucleoside linkages. RNAs having modified backbones include, among others, those that do not have a phosphorus atom in the backbone. For the purposes of this specification, and as sometimes referenced in the art, modified RNAs that do not have a phosphorus atom in their internucleoside backbone can also be considered to be oligonucleosides. In some embodiments of any of the aspects, the modified RNA will have a phosphorus atom in its internucleoside backbone.

Modified RNA backbones can include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those) having inverted polarity wherein the adjacent pairs of nucleoside units are linked 3'-5' to 5'-3' or 2'-5' to 5'-2'. Various salts, mixed salts and free acid forms are also included. Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; others having mixed N, O, S and CH2 component parts, and oligonucleosides with heteroatom backbones, and in particular —CH2-NH—CH2-, —CH2-N(CH3)-O-CH2- [known as a methylene (methylimino) or MMI backbone], —CH2-O—N(CH3)-CH2-, —CH2-N(CH3)-N(CH3)-CH2- and —N(CH3)-CH2-CH2- [wherein the native phosphodiester backbone is represented as —O—P—O—CH2-].

In other RNA mimetics suitable or contemplated for use as agonists or inhibitors, both the sugar and the internucleoside linkage, i.e., the backbone, of the nucleotide units are replaced with novel groups. The base units are maintained for hybridization with an appropriate nucleic acid target compound. One such oligomeric compound, an RNA mimetic that has been shown to have excellent hybridization properties, is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone.

A RNA can also be modified to include one or more locked nucleic acids (LNA). A locked nucleic acid is a nucleotide having a modified ribose moiety in which the ribose moiety comprises an extra bridge connecting the 2' and 4' carbons. This structure effectively "locks" the ribose in the 3'-endo structural conformation. The addition of locked nucleic acids has been shown to increase RNA stability in serum, and to reduce off-target effects (Elmen, J. et al., (2005) Nucleic Acids Research 33(1):439-447; Mook, O R. et al., (2007) Mol Canc Ther 6(3):833-843; Grunweller, A. et al., (2003) Nucleic Acids Research 31(12):3185-3193).

Modified RNAs can also contain one or more substituted sugar moieties. The RNAs, e.g., agonists and/or inhibitors, described herein can include one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C1 to C10 alkyl or C2 to C10 alkenyl and alkynyl. Exemplary suitable modifications include O[(CH2)nO]mCH3, O(CH2).nOCH3, O(CH2)nNH2, O(CH2) nCH3, O(CH2)nONH2, and O(CH2)nON[(CH2)nCH3)]2, where n and m are from 1 to about 10. In some embodiments of any of the aspects, dsRNAs include one of the following at the 2' position: C1 to C10 lower alkyl, substituted lower alkyl, alkaryl, aralkyl, O-alkaryl or O-aralkyl, SH, SCH3, OCN, Cl, Br, CN, CF3, OCF3, SOCH3, SO2CH3, ONO2, NO2, N3, NH2, heterocycloalkyl, heterocycloalkaryl, aminoalkylamino, polyalkylamino, substituted silyl, an RNA cleaving group, a reporter group, an intercalator, a group for improving the pharmacokinetic properties of an RNA, or a group for improving the pharmacodynamic properties of an RNA, and other substituents having similar properties. In some embodiments of any of the aspects, the modification includes a 2' methoxyethoxy (2'-O—CH2CH2OCH3, also known as 2'-O-(2-methoxyethyl) or 2'-MOE) (Martin et al., Helv. Chim. Acta, 1995, 78:486-504) i.e., an alkoxy-alkoxy group. Another exemplary modification is 2'-dimethylaminooxyethoxy, i.e., a O(CH2)2ON(CH3)2 group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—CH2-O-CH2-N(CH2)2, also described in examples herein below.

Other modifications include 2'-methoxy (2'-OCH3), 2'-aminopropoxy (2'-OCH2CH2CH2NH2) and 2'-fluoro (2'-F). Similar modifications can also be made at other positions on the RNA, particularly the 3' position of the sugar on the 3' terminal nucleotide or in 2'-5' linked dsRNAs and the 5' position of 5' terminal nucleotide. RNAs may also have sugar mimetics such as cyclobutyl moieties in place of the pentofuranosyl sugar.

A nucleic acid as described herein can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Certain of these nucleobases are particularly useful for increasing the binding affinity of the nucleic acids featured in the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, 1993, pp. 276-278) and are exemplary base substitutions, even more particularly when combined with 2'-O-methoxyethyl sugar modifications.

The preparation of the modified nucleic acids, backbones, and nucleobases described above are well known in the art.

Another modification of a nucleic acid featured in the invention, e.g., an agonist or inhibitor as described herein, involves chemically linking to the nucleic acid to one or more ligands, moieties or conjugates that enhance the activity, cellular distribution, pharmacokinetic properties, or cellular uptake of the RNA. Such moieties include but are not limited to lipid moieties such as a cholesterol moiety (Letsinger et al., Proc. Natl. Acid. Sci. USA, 1989, 86: 6553-6556), cholic acid (Manoharan et al., Biorg. Med. Chem. Let., 1994, 4:1053-1060), a thioether, e.g., beryl-S-tritylthiol (Manoharan et al., Ann. N.Y. Acad. Sci., 1992, 660:306-309; Manoharan et al., Biorg. Med. Chem. Let., 1993, 3:2765-2770), a thiocholesterol (Oberhauser et al., Nucl. Acids Res., 1992, 20:533-538), an aliphatic chain, e.g., dodecandiol or undecyl residues (Saison-Behmoaras et al., EMBO J, 1991, 10:1111-1118; Kabanov et al., FEBS Lett., 1990, 259:327-330; Svinarchuk et al., Biochimie, 1993, 75:49-54), a phospholipid, e.g., di-hexadecyl-rac-glycerol or triethyl-ammonium 1,2-di-O-hexadecyl-rac-glycero-3-phosphonate (Manoharan et al., Tetrahedron Lett., 1995, 36:3651-3654; Shea et al., Nucl. Acids Res., 1990, 18:3777-3783), a polyamine or a polyethylene glycol chain (Manoharan et al., Nucleosides & Nucleotides, 1995, 14:969-973), or adamantane acetic acid (Manoharan et al., Tetrahedron Lett., 1995, 36:3651-3654), a palmityl moiety (Mishra et al., Biochim. Biophys. Acta, 1995, 1264:229-237), or an octadecylamine or hexylamino-carbonyloxycholesterol moiety (Crooke et al., J. Pharmacol. Exp. Ther., 1996, 277:923-937).

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. lung cancer. The term "treating" includes reducing or alleviating at least one adverse effect or symptom of a condition, disease or disorder associated with a condition. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In some embodiments of any of the aspects, a pharmaceutically acceptable carrier can be a carrier other than water. In some embodiments of any of the aspects, a pharmaceutically acceptable carrier can be a cream, emulsion, gel, liposome, nanoparticle, and/or ointment. In some embodiments of any of the aspects, a pharmaceutically acceptable carrier can be an artificial or engineered carrier, e.g., a carrier that the active ingredient would not be found to occur in in nature.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean ±1%.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 19th Edition, published by Merck Sharp & Dohme Corp., 2011 (ISBN 978-0-911910-19-3); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, 4$^{th}$ ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

One of skill in the art can readily identify a chemotherapeutic agent of use (e.g. see Physicians' Cancer Chemotherapy Drug Manual 2014, Edward Chu, Vincent T. DeVita Jr., Jones & Bartlett Learning; Principles of Cancer Therapy, Chapter 85 in Harrison's Principles of Internal Medicine, 18th edition; Therapeutic Targeting of Cancer Cells: Era of Molecularly Targeted Agents and Cancer Pharmacology, Chs. 28-29 in Abeloff's Clinical Oncology, 2013 Elsevier; and Fischer D S (ed): The Cancer Chemotherapy Handbook, 4th ed. St. Louis, Mosby-Year Book, 2003).

In some embodiments of any of the aspects, the disclosure described herein does not concern a process for cloning human beings, processes for modifying the germ line genetic identity of human beings, uses of human embryos for industrial or commercial purposes or processes for modifying the genetic identity of animals which are likely to cause them suffering without any substantial medical benefit to man or animal, and also animals resulting from such processes.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. A method comprising:
   detecting the level of expression of at least 1 miRNAs selected from the group consisting of:
   miR-146a-5p, miR-324-5p, miR-223-3p, miR-223-5p; hsa-miR-450b-5p, hsa-miR-221-3p, hsa-miR-223-5p, hsa-miR-223-3p, hsa-miR-505-3p, and hsa-miR-582-5p;
   in a sample obtained from a subject.
2. The method of paragraph 1, wherein the level of expression is detected for at least two miRNAs selected from the group consisting of:
   miR-146a-5p, miR-324-5p, miR-223-3p, miR-223-5p; hsa-miR-450b-5p, hsa-miR-221-3p, hsa-miR-223-5p, hsa-miR-223-3p, hsa-miR-505-3p, and hsa-miR-582-5p.
3. The method of paragraph 1, wherein the level of expression is detected for at least three miRNAs selected from the group consisting of:
   miR-146a-5p, miR-324-5p, miR-223-3p, miR-223-5p; hsa-miR-450b-5p, hsa-miR-221-3p, hsa-miR-223-5p, hsa-miR-223-3p, hsa-miR-505-3p, and hsa-miR-582-5p.
4. The method of paragraph 1, wherein the level of expression is detected for at least four miRNAs selected from the group consisting of:
   miR-146a-5p, miR-324-5p, miR-223-3p, miR-223-5p; hsa-miR-450b-5p, hsa-miR-221-3p, hsa-miR-223-5p, hsa-miR-223-3p, hsa-miR-505-3p, and hsa-miR-582-5p.
5. The method of paragraph 1, wherein the level of expression is detected for at least five miRNAs selected from the group consisting of:
   miR-146a-5p, miR-324-5p, miR-223-3p, miR-223-5p; hsa-miR-450b-5p, hsa-miR-221-3p, hsa-miR-223-5p, hsa-miR-223-3p, hsa-miR-505-3p, and hsa-miR-582-5p.
6. The method of paragraph 1, wherein the level of expression is detected for at least six miRNAs selected from the group consisting of:
   miR-146a-5p, miR-324-5p, miR-223-3p, miR-223-5p; hsa-miR-450b-5p, hsa-miR-221-3p, hsa-miR-223-5p, hsa-miR-223-3p, hsa-miR-505-3p, and hsa-miR-582-5p.
7. The method of paragraph 1, wherein the level of expression is detected for at least seven miRNAs selected from the group consisting of:
   miR-146a-5p, miR-324-5p, miR-223-3p, miR-223-5p; hsa-miR-450b-5p, hsa-miR-221-3p, hsa-miR-223-5p, hsa-miR-223-3p, hsa-miR-505-3p, and hsa-miR-582-5p.
8. The method of paragraph 1, wherein the level of expression is detected for at least eight miRNAs selected from the group consisting of:
   miR-146a-5p, miR-324-5p, miR-223-3p, miR-223-5p; hsa-miR-450b-5p, hsa-miR-221-3p, hsa-miR-223-5p, hsa-miR-223-3p, hsa-miR-505-3p, and hsa-miR-582-5p.
9. The method of paragraph 1, wherein the level of expression is detected for at least nine miRNAs selected from the group consisting of:
   miR-146a-5p, miR-324-5p, miR-223-3p, miR-223-5p; hsa-miR-450b-5p, hsa-miR-221-3p, hsa-miR-223-5p, hsa-miR-223-3p, hsa-miR-505-3p, and hsa-miR-582-5p.
10. The method of paragraph 1, wherein the level of expression is detected for miR-146a-5p, miR-324-5p, miR-223-3p, miR-223-5p; hsa-miR-450b-5p, hsa-miR-221-3p, hsa-miR-223-5p, hsa-miR-223-3p, hsa-miR-505-3p, and hsa-miR-582-5p.
11. The method of any of paragraphs 1-10, wherein the level of expression is detected for at least miR-146a-5p, miR-324-5p, miR-223-3p, and miR-223-5p.
12. The method of paragraphs 1-11, wherein the level of expression is detected for at least miR-146a-5p.
13. The method of any of paragraphs 1-12, wherein the subject is a mammal.
14. The method of paragraph 13, wherein the subject is a human.
15. The method of any of paragraphs 1-14, wherein the subject is a a current or former smoker.
16. The method of any of paragraphs 1-15, wherein the sample is a bronchial brushing or nose epithelial sample.
17. The method of any of paragraphs 1-16, wherein the subject is at risk of developing lung cancer.
18. The method of any of paragraphs 1-17, wherein the detecting step comprises sequencing of miRNAs in the sample.
19. The method of any of paragraphs 1-18, wherein the method further comprises detecting the expression level of one or more mRNAs.
20. The method of any of paragraphs 1-19, wherein the expression level of no more than 100 miRNAs and/or mRNAs is detected.

The method of any of paragraphs 1-20, wherein, the method further comprises administering an agonist of at least 1 miRNAs selected from the group consisting of:
   miR-146a-5p, miR-324-5p, miR-223-3p, miR-223-5p; hsa-miR-450b-5p, hsa-miR-221-3p, hsa-miR-223-5p, hsa-miR-223-3p, hsa-miR-505-3p, and hsa-miR-582-5p
to the subject.

21. A method comprising:
    obtaining a sample from a subject; and
    detecting the level of expression of at least 1 miRNAs selected from the group consisting of:
    miR-146a-5p, miR-324-5p, miR-223-3p, miR-223-5p; hsa-miR-450b-5p, hsa-miR-221-3p, hsa-miR-223-5p, hsa-miR-223-3p, hsa-miR-505-3p, and hsa-miR-582-5p;
    in the sample.
22. An assay for detecting lung cancer a subject, the assay comprising:
    subjecting a test sample of a subject to at least one analysis to determine the level of expression of at least 1 miRNAs selected from the group consisting of:
    miR-146a-5p, miR-324-5p, miR-223-3p, miR-223-5p; hsa-miR-450b-5p, hsa-miR-221-3p, hsa-miR-223-5p, hsa-miR-223-3p, hsa-miR-505-3p, and hsa-miR-582-5p;
    wherein an expression level of the at least 1 miRNA which decreased relative to a reference level, indicates the presence of lung cancer.
23. The assay of paragraph 22, wherein the level of expression is detected for at least two miRNAs selected from the group consisting of:
    miR-146a-5p, miR-324-5p, miR-223-3p, miR-223-5p; hsa-miR-450b-5p, hsa-miR-221-3p, hsa-miR-223-5p, hsa-miR-223-3p, hsa-miR-505-3p, and hsa-miR-582-5p.

24. The assay of paragraph 22, wherein the level of expression is detected for at least three miRNAs selected from the group consisting of:
   miR-146a-5p, miR-324-5p, miR-223-3p, miR-223-5p; hsa-miR-450b-5p, hsa-miR-221-3p, hsa-miR-223-5p, hsa-miR-223-3p, hsa-miR-505-3p, and hsa-miR-582-5p.
25. The assay of paragraph 22, wherein the level of expression is detected for at least four miRNAs selected from the group consisting of:
   miR-146a-5p, miR-324-5p, miR-223-3p, miR-223-5p; hsa-miR-450b-5p, hsa-miR-221-3p, hsa-miR-223-5p, hsa-miR-223-3p, hsa-miR-505-3p, and hsa-miR-582-5p.
26. The assay of paragraph 22, wherein the level of expression is detected for at least five miRNAs selected from the group consisting of:
   miR-146a-5p, miR-324-5p, miR-223-3p, miR-223-5p; hsa-miR-450b-5p, hsa-miR-221-3p, hsa-miR-223-5p, hsa-miR-223-3p, hsa-miR-505-3p, and hsa-miR-582-5p.
27. The assay of paragraph 22, wherein the level of expression is detected for at least six miRNAs selected from the group consisting of:
   miR-146a-5p, miR-324-5p, miR-223-3p, miR-223-5p; hsa-miR-450b-5p, hsa-miR-221-3p, hsa-miR-223-5p, hsa-miR-223-3p, hsa-miR-505-3p, and hsa-miR-582-5p.
28. The assay of paragraph 22, wherein the level of expression is detected for at least seven miRNAs selected from the group consisting of:
   miR-146a-5p, miR-324-5p, miR-223-3p, miR-223-5p; hsa-miR-450b-5p, hsa-miR-221-3p, hsa-miR-223-5p, hsa-miR-223-3p, hsa-miR-505-3p, and hsa-miR-582-5p.
29. The assay of paragraph 22, wherein the level of expression is detected for at least eight miRNAs selected from the group consisting of:
   miR-146a-5p, miR-324-5p, miR-223-3p, miR-223-5p; hsa-miR-450b-5p, hsa-miR-221-3p, hsa-miR-223-5p, hsa-miR-223-3p, hsa-miR-505-3p, and hsa-miR-582-5p.
30. The assay of paragraph 22, wherein the level of expression is detected for at least nine miRNAs selected from the group consisting of:
   miR-146a-5p, miR-324-5p, miR-223-3p, miR-223-5p; hsa-miR-450b-5p, hsa-miR-221-3p, hsa-miR-223-5p, hsa-miR-223-3p, hsa-miR-505-3p, and hsa-miR-582-5p.
31. The assay of paragraph 22, wherein the level of expression is detected for miR-146a-5p, miR-324-5p, miR-223-3p, miR-223-5p; hsa-miR-450b-5p, hsa-miR-221-3p, hsa-miR-223-5p, hsa-miR-223-3p, hsa-miR-505-3p, and hsa-miR-582-5p.
32. The assay of any of paragraphs 22-31, wherein the level of expression is detected for at least miR-146a-5p, miR-324-5p, miR-223-3p, and miR-223-5p.
33. The assay of any of paragraphs 22-32, wherein the level of expression is detected for at least miR-146a-5p.
34. The assay of any of paragraphs 22-33, wherein the subject is a mammal.
35. The assay of any of paragraphs 22-34, wherein the subject is a human.
36. The assay of any of paragraphs 22-35, wherein the subject is a a current or former smoker.
37. The assay of any of paragraphs 22-36, wherein the sample is a bronchial brushing or nose epithelial sample.
38. The assay of any of paragraphs 22-37, wherein the subject is at risk of developing lung cancer.
39. The assay of any of paragraphs 22-38, wherein the detecting step comprises sequencing of miRNAs in the sample.
40. The assay of any of paragraphs 22-39, wherein the method further comprises detecting the expression level of one or more mRNAs.
41. The assay of any of paragraphs 22-40, wherein the expression level of no more than 100 miRNAs and/or mRNAs is detected.
   The method of any of paragraphs 1-20, wherein, the method further comprises administering an agonist of at least 1 miRNAs selected from the group consisting of:
   miR-146a-5p, miR-324-5p, miR-223-3p, miR-223-5p; hsa-miR-450b-5p, hsa-miR-221-3p, hsa-miR-223-5p, hsa-miR-223-3p, hsa-miR-505-3p, and hsa-miR-582-5p
   to the subject.
42. A method of treating lung cancer in a subject in need thereof, the method comprising administering of the subject an agonist of at least 1 miRNAs selected from the group consisting of:
   miR-146a-5p, miR-324-5p, miR-223-3p, miR-223-5p; hsa-miR-450b-5p, hsa-miR-221-3p, hsa-miR-223-5p, hsa-miR-223-3p, hsa-miR-505-3p, and hsa-miR-582-5p.
   to the subject.

Some embodiments of the technology described herein can be defined according to any of the following numbered paragraphs:
1. A method of treating lung cancer in a subject in need thereof, the method comprising administering to the subject an agonist of at least 1 miRNA selected from the group consisting of:
   miR-146a-5p, miR-324-5p, miR-223-3p, miR-223-5p; miR-450b-5p, miR-221-3p-miR-505-3p, and miR-582-5p.
   to the subject.
2. A method of treating lung cancer in a subject in need thereof, the method comprising administering to the subject an agonist of at least 1 miRNA selected from Table 10 and/or an inhibitor of at least 1 miRNA selected from Table 11 to the subject.
3. The method of any of paragraphs 1-2, wherein the administering step comprises the administration of a vector comprising a nucleic acid encoding the agonist and/or inhibitor.
4. A method comprising:
   detecting the level of expression of at least 1 miRNA selected from the group consisting of:
      miR-146a-5p, miR-324-5p, miR-223-3p, miR-223-5p; miR-450b-5p, miR-221-3p-miR-505-3p, and miR-582-5p;
   in a sample obtained from a subject.
5. A method comprising:
   obtaining a sample from a subject; and
   detecting the level of expression of at least 1 miRNAs selected from the group consisting of:
      miR-146a-5p, miR-324-5p, miR-223-3p, miR-223-5p; miR-450b-5p, miR-221-3p-miR-505-3p, and miR-582-5p;
   in the sample.
6. The method of paragraph 4 or 5, wherein the level of expression is detected for at least two miRNAs selected from the group consisting of:

miR-146a-5p, miR-324-5p, miR-223-3p, miR-223-5p; miR-450b-5p, miR-221-3p-miR-505-3p, and miR-582-5p.

7. The method of paragraph 4 or 5, wherein the level of expression is detected for at least three miRNAs selected from the group consisting of:
miR-146a-5p, miR-324-5p, miR-223-3p, miR-223-5p; miR-450b-5p, miR-221-3p-miR-505-3p, and miR-582-5p.

8. The method of paragraph 4 or 5, wherein the level of expression is detected for at least four miRNAs selected from the group consisting of:
miR-146a-5p, miR-324-5p, miR-223-3p, miR-223-5p; miR-450b-5p, miR-221-3p-miR-505-3p, and miR-582-5p.

9. The method of paragraph 4 or 5, wherein the level of expression is detected for at least five miRNAs selected from the group consisting of:
miR-146a-5p, miR-324-5p, miR-223-3p, miR-223-5p; miR-450b-5p, miR-221-3p-miR-505-3p, and miR-582-5p.

10. The method of paragraph 4 or 5, wherein the level of expression is detected for at least six miRNAs selected from the group consisting of:
miR-146a-5p, miR-324-5p, miR-223-3p, miR-223-5p; miR-450b-5p, miR-221-3p-miR-505-3p, and miR-582-5p.

11. The method of paragraph 4 or 5, wherein the level of expression is detected for at least seven miRNAs selected from the group consisting of:
miR-146a-5p, miR-324-5p, miR-223-3p, miR-223-5p; miR-450b-5p, miR-221-3p-miR-505-3p, and miR-582-5p.

12. The method of paragraph 4 or 5, wherein the level of expression is detected for miR-146a-5p, miR-324-5p, miR-223-3p, miR-223-5p; miR-450b-5p, miR-221-3p-miR-505-3p, and miR-582-5p.

13. The method of any of paragraphs 4-12, wherein the level of expression is detected for at least miR-146a-5p, miR-324-5p, miR-223-3p, and miR-223-5p.

14. The method of paragraphs 4-13, wherein the level of expression is detected for at least miR-146a-5p.

15. A method comprising:
detecting the level of expression of at least 1 miRNA selected from Table 10 and/or Table 11 in a sample obtained from a subject.

16. A method comprising:
obtaining a sample from a subject; and
detecting the level of expression of at least 1 miRNA selected from Table 10 and/or Table 11 in the sample.

17. The method of any of paragraphs 1-16, wherein the subject is a mammal.

18. The method of paragraph 17, wherein the subject is a human.

19. The method of any of paragraphs 1-18, wherein the subject is a current or former smoker.

20. The method of any of paragraphs 4-19, wherein the sample is a bronchial brushing or nose epithelial sample.

21. The method of any of paragraphs 4-20, wherein the subject is at risk of developing lung cancer.

22. The method of any of paragraphs 4-21, wherein the detecting step comprises sequencing of miRNAs in the sample.

23. The method of any of paragraphs 4-22, wherein the method further comprises detecting the expression level of one or more mRNAs.

24. The method of any of paragraphs 4-23, wherein the expression level of no more than 100 miRNAs and/or mRNAs is detected.

25. The method of any of paragraphs 4-24, wherein, the method further comprises administering an agonist of at least 1 miRNA selected from Table 10 or an inhibitor of at least one miRNA selected from Table 11 to the subject.

26. The method of any of paragraphs 44-25, wherein, the method further comprises administering an agonist of at least 1 miRNA selected from the group consisting of:
miR-146a-5p, miR-324-5p, miR-223-3p, miR-223-5p; miR-450b-5p, miR-221-3p-miR-505-3p, and miR-582-5p
to the subject.

27. An assay for detecting lung cancer a subject, the assay comprising:
subjecting a test sample of a subject to at least one analysis to determine the level of expression of at least 1 miRNAs selected from the group consisting of:
miR-146a-5p, miR-324-5p, miR-223-3p, miR-223-5p; miR-450b-5p, miR-221-3p-miR-505-3p, and miR-582-5p;
wherein an expression level of the at least 1 miRNA which decreased relative to a reference level, indicates the presence of lung cancer.

28. The assay of paragraph 27, wherein the level of expression is detected for at least two miRNAs selected from the group consisting of:
miR-146a-5p, miR-324-5p, miR-223-3p, miR-223-5p; miR-450b-5p, miR-221-3p-miR-505-3p, and miR-582-5p.

29. The assay of paragraph 27, wherein the level of expression is detected for at least three miRNAs selected from the group consisting of:
miR-146a-5p, miR-324-5p, miR-223-3p, miR-223-5p; miR-450b-5p, miR-221-3p-miR-505-3p, and miR-582-5p.

30. The assay of paragraph 27, wherein the level of expression is detected for at least four miRNAs selected from the group consisting of:
miR-146a-5p, miR-324-5p, miR-223-3p, miR-223-5p; miR-450b-5p, miR-221-3p-miR-505-3p, and miR-582-5p.

31. The assay of paragraph 27, wherein the level of expression is detected for at least five miRNAs selected from the group consisting of:
miR-146a-5p, miR-324-5p, miR-223-3p, miR-223-5p; miR-450b-5p, miR-221-3p-miR-505-3p, and miR-582-5p.

32. The assay of paragraph 27, wherein the level of expression is detected for at least six miRNAs selected from the group consisting of:
miR-146a-5p, miR-324-5p, miR-223-3p, miR-223-5p; miR-450b-5p, miR-221-3p-miR-505-3p, and miR-582-5p.

33. The assay of paragraph 27, wherein the level of expression is detected for at least seven miRNAs selected from the group consisting of:
miR-146a-5p, miR-324-5p, miR-223-3p, miR-223-5p; miR-450b-5p, miR-221-3p-miR-505-3p, and miR-582-5p.

34. The assay of paragraph 27, wherein the level of expression is detected miR-146a-5p, miR-324-5p, miR-223-3p, miR-223-5p; miR-450b-5p, miR-221-3p-miR-505-3p, and miR-582-5p.

35. The assay of any of paragraphs 27-34, wherein the level of expression is detected for at least miR-146a-5p, miR-324-5p, miR-223-3p, and miR-223-5p.
36. The assay of any of paragraphs 27-35, wherein the level of expression is detected for at least miR-146a-5p.
37. An assay for detecting lung cancer a subject, the assay comprising:
    subjecting a test sample of a subject to at least one analysis to determine the level of expression of at least 1 miRNA selected from Table 10 and/or Table 11;
    wherein an expression level of the at least 1 miRNA of Table 10 which is decreased relative to a reference level or an expression level of the at least 1 miRNA of Table 11 which is increased relative to a reference level, indicates the presence of lung cancer.
38. The assay of any of paragraphs 27-37, wherein the subject is a mammal.
39. The assay of any of paragraphs 27-38, wherein the subject is a human.
40. The assay of any of paragraphs 27-39, wherein the subject is a current or former smoker.
41. The assay of any of paragraphs 27-40, wherein the sample is a bronchial brushing or nose epithelial sample.
42. The assay of any of paragraphs 27-41, wherein the subject is at risk of developing lung cancer.
43. The assay of any of paragraphs 27-42, wherein the detecting step comprises sequencing of miRNAs in the sample.
44. The assay of any of paragraphs 27-43, wherein the method further comprises detecting the expression level of one or more mRNAs.
45. The assay of any of paragraphs 27-44, wherein the expression level of no more than 100 miRNAs and/or mRNAs is detected.
46. The assay of any of paragraphs 27-45, wherein the method further comprises administering an agonist of at least 1 miRNA selected from Table 10 and/or an inhibitor of at least 1 miRNA selected from Table 11 to the subject.
47. The assay of any of paragraphs 27-46, wherein the method further comprises administering an agonist of at least 1 miRNAs selected from the group consisting of:
    miR-146a-5p, miR-324-5p, miR-223-3p, miR-223-5p; miR-450b-5p, miR-221-3p-miR-505-3p, and miR-582-5p
    to the subject.

Some embodiments of the technology described herein can be defined according to any of the following numbered paragraphs:
1. A method of treating lung cancer in a subject in need thereof, the method comprising
    administering to the subject an agonist of at least 1 miRNA selected from Table 10 or an inhibitor of at least 1 miRNA selected from Table 11 to the subject.
2. The method of paragraph 1, wherein the subject is administered an agonist of at least 1 miRNA selected from the group consisting of:
    miR-146a-5p, miR-324-5p, miR-223-3p, miR-223-5p; miR-450b-5p, miR-221-3p-miR-505-3p, and miR-582-5p.
3. The method of paragraph 1, wherein the administering step comprises the administration of a vector comprising a nucleic acid encoding the agonist and/or inhibitor.
4. The method of paragraph 1, wherein the subject is a human.
5. The method of paragraph 1, wherein the subject is a current or former smoker.
6. A method of treating lung cancer in a subject in need thereof, the method comprising administering a treatment for lung cancer to a subject determined to have a level of expression of at least 1 miRNAs selected from the group consisting of:
    miR-146a-5p, miR-324-5p, miR-223-3p, miR-223-5p; miR-450b-5p, miR-221-3p-miR-505-3p, and miR-582-5p;
    in a sample obtained from the subject which is decreased relative to a reference level.
7. The method of paragraph 6, further comprising the first steps of obtaining a sample from a subject; and determining the level of expression of the at least 1 miRNA; and administering a treatment for lung cancer if the level of expression of the at least 1 miRNA is decreased relative to a reference level.
8. The method of paragraph 6, wherein the level of expression is detected for at least two miRNAs selected from the group consisting of:
    miR-146a-5p, miR-324-5p, miR-223-3p, miR-223-5p; miR-450b-5p, miR-221-3p-miR-505-3p, and miR-582-5p.
9. The method of paragraph 6, wherein the level of expression is detected for at least three miRNAs selected from the group consisting of:
    miR-146a-5p, miR-324-5p, miR-223-3p, miR-223-5p; miR-450b-5p, miR-221-3p-miR-505-3p, and miR-582-5p.
10. The method of paragraph 6, wherein the level of expression is detected for at least four miRNAs selected from the group consisting of:
    miR-146a-5p, miR-324-5p, miR-223-3p, miR-223-5p; miR-450b-5p, miR-221-3p-miR-505-3p, and miR-582-5p.
11. The method of paragraph 6, wherein the level of expression is detected for at least five miRNAs selected from the group consisting of:
    miR-146a-5p, miR-324-5p, miR-223-3p, miR-223-5p; miR-450b-5p, miR-221-3p-miR-505-3p, and miR-582-5p.
12. The method of paragraph 6, wherein the level of expression is detected for at least six miRNAs selected from the group consisting of:
    miR-146a-5p, miR-324-5p, miR-223-3p, miR-223-5p; miR-450b-5p, miR-221-3p-miR-505-3p, and miR-582-5p.
13. The method of paragraph 6, wherein the level of expression is detected for at least seven miRNAs selected from the group consisting of:
    miR-146a-5p, miR-324-5p, miR-223-3p, miR-223-5p; miR-450b-5p, miR-221-3p-miR-505-3p, and miR-582-5p.
14. The method of paragraph 6, wherein the level of expression is detected for miR-146a-5p, miR-324-5p, miR-223-3p, miR-223-5p; miR-450b-5p, miR-221-3p-miR-505-3p, and miR-582-5p.
15. The method of paragraph 6, wherein the level of expression is detected for at least miR-146a-5p, miR-324-5p, miR-223-3p, and miR-223-5p.
16. The method of paragraph 6, wherein the level of expression is detected for at least miR-146a-5p.
17. The method of paragraph 6, wherein the sample is a bronchial brushing or nose epithelial sample.
18. The method of paragraph 6, wherein the method further comprises detecting the expression level of one or more mRNAs.

19. The method of paragraph 6, wherein the expression level of no more than 100 miRNAs and/or mRNAs is detected.
20. The method of paragraph 6, wherein the treatment for lung cancer comprises administering an agonist of at least 1 miRNA selected from the group consisting of:
    miR-146a-5p, miR-324-5p, miR-223-3p, miR-223-5p; miR-450b-5p, miR-221-3p-miR-505-3p, and miR-582-5p
    to the subject.

EXAMPLES

Example 1

Bronchial brushings were collected from current and former smokers undergoing bronchoscopy for suspect lung cancer across 28 medical centers as part of the AEGIS clinical trials. MicroRNA expression was profiled via small RNA sequencing for 347 patients for which gene expression data was also available. Described hereins are alterations in microRNA expression in the cytologically normal mainstem bronchus of smokers with lung cancer. Importantly, performance of existing bronchial gene-expression biomarkers for lung cancer can be significantly improved by incorporating the expression of miR-146a-5p.

The methods described herein relate to the the diagnosis, prognosis, detection, and/or treatment of lung cancer detection using bronchial brushings collected from current and former smokers undergoing bronchoscopy for suspected lung cancer.

In some embodiments, by addition of microRNA expression, we improve the performance of Percepta, the first commercially available bronchial gene expression biomarker for lung cancer detection. In some embodiments, the methods described herein can be used in combination with, or concurrently with PERCEPTA and/or the methods described in International Patent Publication WO2005/000098; which is incorporated by reference herein in its entirety.

Described herein are 8 cancer-associated microRNAs which can be microRNA therapeutic targets for lung cancer. These microRNAs are under-expressed in lung cancer and can act as dysregulated tumor suppressors. It is contemplated herein that their targets can reveal new underlying mechanisms of lung cancer development.

Demonstrated herein is the use of bronchial microRNA data for lung cancer detection. microRNA data provides additional independent information to gene expression, that can be used to improve lung cancer biomarkers.

Bronchial miR-146a-5p expression adds independent information to existing bronchial gene expression biomarker(s). This microRNA is known to control immune function, hematopoiesis and different cancer mechanisms.

The biomarkers described herein can be used in combination with targeted therapy to monitor the evolution the airway field of injury.

In some embodiments, described herein are integrative biomarkers of gene and microRNA expression. The proposed approach can further be extended by integrating multiple datatypes, such as gene and protein expression, epigenetic data, somatic mutations, copy number data, etc.

In some embodiments, described herein is a clinically relevant test for lung cancer detection using bronchial microRNA and gene expression from current and former smokers undergoing bronchoscopy for suspected lung. This test improves the performance of Percepta, the first commercially available bronchial gene expression biomarker for lung cancer detection. Percepta's AUC is significantly improved (p-value 0.025).

Bronchoscopy is a low risk clinical procedure, therefore the methods described herein are a less invasive test compared to biopsy or surgery. Additionally, the methods described herein are relatively cheap compared to CT screening, biopsy or surgery and moving the test into the nose tissue will make the procedure even less invasive.

Gene expression alterations in normal appearing epithelial cells from the mainstem bronchus can be used as an early detection biomarker for lung cancer among current and former smokers with suspect disease. It is contemplated herein that microRNA expression in bronchial epithelial cells is associated with the presence of lung cancer and that in some embodiments, integrating microRNA and gene expression could yield a more robust classifier.

As demonstrated herein, there are alterations in microRNA expression in the cytologically normal ainstem bronchus of smokers with lung cancer. In addition, we identified microRNAs which regulate some of the bronchial gene-expression changes previously associated with lung cancer. Importantly, we found that the performance of an existing bronchial gene-expression biomarker for lung cancer can be improved by incorporating microRNA expression.

Patients under suspicion of having lung cancer are increasingly being screened with CT, leading to an increase in the number of discovered solitary pulmonary nodules. Depending on the patient's history and preferences, the risk of cancer and the risk of surgery, as well as the characteristics of the nodule, these lesions are either serially monitored with imaging or the patients undergo invasive evaluation. To facilitate this decision, we recently developed [1] and validated [2] a gene expression based classifier that distinguishes between smokers with and without lung cancer using mRNA isolated from cytologically normal cells in the mainstem bronchus. The fact that some genes are differentially expressed by cancer status in the normal appearing airway supports the idea of an airway molecular field of injury spanning the respiratory tract [3]. We hypothesize that bronchial microRNA expression changes, in addition to mRNA changes, may also be associated with the presence of lung cancer and that integrating microRNA with gene expression information could yield a more robust classifier.

MicroRNAs are a class of small noncoding RNAs that repress the expression of their targets by binding to 3' UTR complementary strands. microRNAs have been shown to be associated with various cancers and have been previously associated with the airway molecular field of injury. In addition, microRNAs are more stable molecules and easier to measure in degraded tissues than mRNAs [4].

Here we extend and improve the mRNA-based biomarker [1], [2] through the exploration of cancer-related microRNAs differentially expressed in the airway wide field of injury. Moreover, we aim to explain some of the mRNA expression changes seen in the airway by identifying the miRNAs regulating these cancer related changes.

REFERENCES

[1] Duncan H Whitney, Michael R Elashoff, Kate Porta-Smith, Adam C Gower, Anil Vachani, J Scott Ferguson, Gerard A Silvestri, Jerome S Brody, Marc E Lenburg and Avrum Spira. Derivation of a bronchial genomic classifier for lung cancer in a prospective study of patients undergoing diagnostic bronchoscopy. BMC Medical Genomics. 8:18. 2015.

[2] Gerard A. Silvestri, Anil Vachani, Duncan Whitney, Michael Elashoff, Kate Porta Smith, J. Scott Ferguson, Ed Parsons, Nandita Mitra, Jerome Brody, Marc E. Lenburg, and Avrum Spira, for the AEGIS Study Team, A Bronchial Genomic Classifier for the Diagnostic Evaluation of Lung Cancer. The New England Journal of Medicine. 2015. DOI: 10.1056/NEJMoa1504601.

[3] Avrum Spira, Jennifer E Beane, Vishal Shah, Katrina Steiling, Gang Liu, Frank Schembri, Sean Gilman, Yves-Martine Dumas, Paul Calner, Paola Sebastiani, Sriram Sridhar, John Beamis, Carla Lamb, Timothy Anderson, Norman Gerry, Joseph Keane, Marc E Lenburg and Jerome S Brody. Airway epithelial gene expression in the diagnostic evaluation of smokers with suspect lung cancer. Nature Medicine. 13(3): 361-366. 2007.

[4] Etheridge A. et al. Extracellular microRNA: a new source of biomarkers. Mutat Res. 717(1-2). 2011.

[5] Perdomo C. et al. MicroRNA 4423 is a primate-specific regulator of airway epithelial cell differentiation and lung carcinogenesis. PNAS. 110(47): 18946-51. 2013.

[6] Frank Schembri, Sriram Sridhar, Catalina Perdomo, Adam M. Gustafson, Xiaoling Zhang, Ayla Ergun, Jining Lu, Gang Liu, Xiaohui Zhang, Jessica Bowers, Cyrus Vaziri, Kristen Ott, Kelly Sensinger, James J. Collins, Jerome S. Brody, Robert Getts, Marc E. Lenburg, Avrum Spira. MicroRNAs as modulators of smoking-induced gene expression changes in human airway epithelium. PNAS. 106(7): 2319-2324. 2009.

[7] Catuogno S. et al. miR-34c may protect lung cancer cells from paclitaxel-induced apoptosis. Oncogene. 32(3). 2013.

[8] Chou Y. T. et al. EGFR promotes lung tumorigenesis by activating miR-7 through a Ras/ERK/Myc pathway that targets the Ets2 transcriptional repressor ERF. Cancer Res. 70(21):8822-31. 2010.

[9] Krysan K. et al. PGE2 driven expression of c-Myc and oncomiR-17-92 contributes to apoptosis resistance in NSCLC. Mol. Cancer Res. 12(5):765-74. 2014.

[10] Nian W. et al. miR-223 functions as a potent tumor suppressor of the Lewis lung carcinoma cell line by targeting insulin-like growth factor-1 receptor and cyclin-dependent kinase 2. Oncol. Lett. 6(2). 2013.

[11] Shen J. et al. Plasma microRNAs as potential biomarkers for non-small-cell lung cancer. Lab. Invest. 91(4):579-87. 2011.

[12] Zheng D. et al. Plasma microRNAs as novel biomarkers for early detection of lung cancer. Int. J. Clin. Exp. Pathol. 4(6):575-86. 2011.

[13] Shinuk Kim, Taesung Park, Mark Kon. Cancer survival classification using integrated data sets and intermediate information. Artificial Intelligence in Medicine. 62(1). 23-31. 2014.

[14] Brase J. C. et al. Serum microRNAs as non-invasive biomarkers for cancer. Mol. Cancer. 9(306). 2010.

[15] Berindan-Neagoe I. and Calin G. A. Molecular Pathways: microRNAs. Cancer Cells. and Microenvironment. Clin. Cancer Res. 20(24):6247-53. 2014.

[16] Jiang F. et al. MiR-125b promotes proliferation and migration of type II endometrial carcinoma cells through targeting TP53INP1 tumor suppressor in vitro and in vivo. BMC Cancer. 11(425). 2011.

[17] Mitchell P. S. et al. Circulating microRNAs as stable blood-based markers for cancer detection. PNAS. 105 (30):10513-10518. 2008.

[18] Nygaard S. et al. Identification and analysis of miRNAs in human breast cancer and teratoma samples using deep sequencing. BMC Med. Genomics. 2(35). 2009.

[19] Taylor D. D. and Gercel-Taylor C. MicroRNA signatures of tumor-derived exosomes as diagnostic biomarkers of ovarian cancer. Gynecol. Oncol. 110(1):13-21. 2008.

[20] Labbaye C. and Testa U., The emerging role of MIR-146A in the control of hematopoiesis, immune function and cancer. Journal of Hematology and Oncology. 5(13). 2012.

Methods:

Using bronchial brushings collected from current and former smokers undergoing bronchoscopy for suspected lung cancer across 28 medical centers as part of the AEGIS clinical trials, we profiled microRNA expression via small RNA sequencing for 347 patients for which gene expression data was also available (Silvestri et al., NEJM 2015) and (BMC Medical Genomics 2015). First, we selected cancer-associated microRNAs by linear modeling. Then, we explored the correlations between expression of these microRNAs and their predicted mRNA targets. Lastly, we tested whether cancer-associated microRNA features improved the established bronchial gene-expression classifier proposed in (Silvestri et al., NEJM 2015) and (Whitney et al., BMC Medical Genomics 2015).

We developed the classifier using the following approach. First, we calculated the prediction scores of the gene expression classifier proposed in (Silvestri et al., NEJM 2015) and (Whitney et al., BMC Medical Genomics 2015) using the subset of samples with matched mRNA and microRNA data. The discovery set (138 samples) is a subset of the patients used to train the gene expression classifier and the test set (203 samples) is a subset of the test cohorts from (Silvestri et al., NEJM 2015). The patient scores were obtained using a logistic regression model which aggregates information from 17 most representative cancer-associated genes, patient's age, and genomic correlates of smoking status, pack years, and gender [18]. Then, we integrated these scores with the expression of a single microRNA. We built a logistic regression model with two variables, the microRNA expression (e.g. miR-146a-5p) and gene-expression classifier score. Next, we trained the weights of the logistic regression in the training set and tested the performance of this integrated score in the test set. The logistic regression model was implemented using cv.glmnet( ) function from glmnet R package. By training the weights of the logistic regression in the discovery set, we obtained the following values: $\beta_1=1.8480041$, $\beta_2=4.3879703$, $\beta_3=-0.3724577$. To evaluate the new classifier we calculated performance metrics including the area under the receiver operating characteristic curve (AUC), the specificity, and the negative predictive value at 90% sensitivity. To compare the ROC curves of gene expression classifier and the improved predictor, we used the DeLong test from the pROC R package.

Results: We found that expression profiles of 42 microRNAs were associated with cancer status in the training set ($p<0.05$). Then we investigated the gene targets of the top differentially expressed microRNAs (FDR<0.2), such as miR-146a-5p, miR-324-5p, miR-223-3p, miR-223-5p. The expression values of these microRNAs were significantly negatively correlated with the expression of their predicted mRNA targets, compared to all microRNAs in the dataset ($p<0.05$). Their gene targets were enriched mainly in cancer associated pathways.

Furthermore, six microRNAs target one or more genes previously established to have cancer-associated expression. These microRNAs are: hsamiR-450b-5p, hsa-miR-221-3p, hsa-miR-223-5p, hsa-miR-223-3p, hsa-miR-505-3p, hsa-miR-582-5p. Their gene targets play roles in retinoic acid metabolism, cell cycle signaling and submucosal gland markers. Moreover, we find that addition of miR-146a-5p, one of the top differentially expressed microRNAs whose expression decreases in the bronchial epithelium of cancer patients, to the existing gene expression biomarker significantly improves the classifier's performance (AUC) in the 203-test set (p-value 0.025). The proposed integrative miRNA-mRNA biomarker performs with an AUC of 0.71 in the test set.

In this study we have established that there are alterations in microRNA expression in the cytologically normal mainstem bronchus of smokers with lung cancer. Additionally, we have shown that microRNA data provides additional information to gene expression data and thus can be used to improve lung cancer biomarkers.

Top four differentially expressed microRNAs which are significantly associated with lung cancer (FDR<0.2) are the following: miR-146a-5p, miR-324-5p, miR-223-3p, miR-223-5p. This finding is novel, since these microRNAs have not been previously associated with the airway field of injury.

Moreover, six differentially expressed microRNAs (p<0.05), such as hsa-miR-450b-5p, hsa-miR-221-3p, hsa-miR-223-5p, hsa-miR-223-3p, hsa-miR-505-3p, hsa-miR-582-5p, regulate bronchial gene-expression changes previously associated with lung cancer. This is the first time these microRNAs are associated with mRNA expression changes in the airway field of injury.

Importantly, we found that the performance of an existing bronchial gene-expression biomarker for lung cancer, previously proposed and tested in (Silvestri et al., NEJM 2015) and (BMC Medical Genomics 2015), is significantly improved by incorporating miR-146a-5p expression (p=0.025). This finding is also novel since miR-146a-5p expression has not been previously shown to improve lung cancer detection Example 2

Gene expression alterations in normal-appearing bronchial epithelial cells can serve as a lung cancer detection biomarker in smokers. Given that miRNAs regulate airway gene expression responses to smoking, it was evaluated whether miRNA expression is also altered in the bronchial epithelium of smokers with lung cancer. Using epithelial brushings from the mainstem bronchus of patients undergoing bronchoscopy for suspected lung cancer (as part of the AEGIS-1/2 clinical trials), miRNA expression was profiled via small-RNA sequencing from 347 current and former smokers for which gene expression data were also available. Patients were followed for one year postbronchoscopy until a final diagnosis of lung cancer (n=194) or benign disease (n=153) was made. Following removal of 6 low-quality samples, 138 patients (AEGIS-1) were used as a discovery set to identify four miRNAs (miR-146a-5p, miR-324-5p, miR-223-3p, and miR-223-5p) that were downregulated in the bronchial airway of lung cancer patients (ANOVA P<0.002, FDR<0.2). The expression of these miRNAs is significantly more negatively correlated with the expression of their mRNA targets than with the expression of other nontarget genes (K-S P<0.05). Furthermore, these mRNA targets are enriched among genes whose expression is elevated in cancer patients (GSEA FDR<0.001). Finally, it was found that the addition of miR-146a-5p to an existing mRNA biomarker for lung cancer significantly improves its performance (AUC) in the 203 samples (AEGIS-1/2) serving as an independent test set (DeLong P<0.05). These findings indicate that there are miRNAs whose expression is altered in the cytologically normal bronchial epithelium of smokers with lung cancer, and that they can regulate cancer-associated gene expression differences.

Lung cancer remains the leading cause of cancer-related death in the United States and the world due, in large part, to the inability to detect the disease at its earliest and curable stage. Once a pulmonary lesion is identified, physicians must decide between CT surveillance versus airway/lung biopsy. When biopsy is required, the approach can include bronchos-copy, transthoracic needle biopsy (TTNB), or surgical lung biopsy (SLB). The choice among these procedures is determined on the basis of considerations such as lesion size and location, the presence of adenopathy, the risk associated with the procedure, and local expertise. Although bronchoscopy is relatively safe (less than 1% of procedures complicated by pneumothorax; ref. 1), this procedure is limited by its sensitivity (from 34% to 88%), depending on the location and size of the lesion (2). Even with newer bronchoscopic guidance techniques, the sensitivity for the detection of lung cancer is below 70% for peripheral lesions (3).

A nondiagnostic bronchoscopy in this setting leads to a clinical dilemma as to which of these patients should undergo further invasive diagnostic testing (TTNB or SLB). To facilitate this clinical decision, a gene expression—based classifier was developed and validated that distinguishes between smokers with and without lung cancer using mRNA isolated from cytologically normal cells in the mainstem bronchus (4, 5). This biomarker can improve the diagnostic sensitivity of bronchoscopy for lung cancer detection.

The ability to identify gene expression changes associated with cancer status in the normal appearing airway supports the idea of an airway molecular field of injury spanning the respiratory tract (6). In this current study, the field of injury concept was expanded to miRNAs. miRNAs are a class of small, noncoding RNAs that repress gene expression and protein translation of their targets by complementary binding to the 3' UTR of RNA transcripts. In addition, compared with mRNAs, miRNAs are thought to be more stable molecules, making them more easily measured in degraded tissues (7). Previous studies have shown that smoking alters the expression of miRNAs in the bronchial airway epithelium (8, 9). It was contemplated herein that similar to mRNA, there might also be miRNA expression changes associated with the presence of lung cancer in bronchial epithelium from the mainstem bronchus that may play a role in regulating cancer-associated gene expression differences and that integrating miRNA with gene expression could improve lung cancer detection.

Materials and Methods

Patient Selection

As previously described, over 1,000 current and former smokers undergoing bronchoscopy for suspected lung cancer were enrolled in the Airway Epithelial Gene Expression in the Diagnosis of Lung Cancer (AEGIS) trials, two independent, prospective, multicenter, observational studies (registered as NCT01309087 and NCT00746759; refs. 4, 5). Exclusion criteria for patients enrolled in AEGIS trials were age less than 21 years, no history of smoking (defined as having smoked <100 cigarettes), and a concurrent cancer diagnosis or history of lung cancer. All study protocols were approved by the Institutional Review Board at each medical center, and written informed consent was obtained from all patients prior to enrollment. Patients were followed prospectively for up to one year post-bronchoscopy until a final diagnosis was obtained.

In this study, miRNA expression was profiled via small RNA sequencing for 347 AEGIS patients. In choosing patients to include in our study, we were limited by patients with a benign diagnosis and matched them approximately 1:1 with patients diagnosed with lung cancer. Moreover, it was attempted to balance the cases and controls for smoking status, cumulative smoke exposure (pack-years), gender, and age. For all of the samples selected for small RNA sequencing, gene expression profiling of the large RNA fraction had been performed previously using Affymetrix Human Gene 1.0 ST arrays (4, 5) and was available for data integration.

138 (~40%) samples were assigned from AEGIS-1 to be used as a discovery set (Table 2); these samples were drawn exclusively from the training set previously used to develop the gene expression classifier (4, 5). The remaining 203 samples comprise a test set (Table 2) and consist exclusively of samples from the AEGIS-1 (n=133) and AEGIS-2 (n=70) test sets that were previously used to validate the gene expression classifier (5).

TABLE 2

| Patient Demographics | Discovery set n = 138 | Test set n = 203 |
|---|---|---|
| Cancer status (n)[a] | | |
| Lung cancer | 88 | 103 |
| Benign disease | 50 | 100 |
| Gender (n) | | |
| Females | 62 | 84 |
| Males | 76 | 119 |
| Age (SD; n) | 59 (11; 138) | 59 (10; 203) |
| Smoking status (n) | | |
| Current | 46 | 88 |
| Former | 92 | 115 |
| Cumutative smoke exposure- pack-yr. (SD; n) | 36 (24; 137) | 37 (29; 199) |
| Race (n) | | |
| White | 109 | 149 |
| Black | 24 | 46 |
| Unknown | 5 | 8 |
| Lesion size (n) | | |
| <3 cm | 52 | 71 |
| ≥3 cm | 58 | 91 |
| Infiltrate | 15 | 31 |
| Unknown | 11 | 10 |
| Histology (n) | | |
| NSCLC | 72 | 79 |
| NSCLC stage | | |
| I | 11 | 16 |
| II | 3 | 5 |
| III | 15 | 19 |
| IV | 29 | 26 |
| Not specified | 14 | 13 |
| NSCLC subtype | | |
| Adenocarcinoma | 31 | 34 |
| Squamous | 27 | 25 |
| Large cell | 2 | 4 |
| Not specified | 12 | 16 |
| SCLC | 16 | 21 |
| SCLC stage | | |
| Limited | 4 | 8 |
| Extensive | 8 | 12 |
| Not specified | 4 | 1 |
| Uncertain histology | 0 | 3 |
| Diagnosis of benign disease (n) | | |
| Resolution or stability | 11 | 26 |
| Alternative diagnosis | 39 | 74 |
| Type of alternative diagnosis | | |
| Sarcoidosis | 9 | 17 |
| Inflammation | 3 | 2 |
| Fibrosis | 1 | 1 |
| Infection | 8 | 14 |
| Other | 18 | 40 |

NOTE:
n indicates number of patients with available, clinical data.
Abbreviations:
NSCLC, non-small cell lung cancer; SCLC, small-cell lung cancer.
[a]$P < 0.05$.

High-Throughput Sequencing of Small RNA

On the basis of previous work on the effect of multiplexing on miRNA expression quantitation (10), 347 samples were sequenced in three batches by multiplexing 12 samples per lane on an Illumina HiSeq 2000™. A total of 200 ng of total RNA from each sample was used for library preparation. The TruSeq Small RNA Sample Prep Kit™ (Illumina) was used for the first batch, while the NEBNext Multiplex Small RNA Library Prep Set™ (Illumina) was used for the second and third batches. RNA adapters were ligated to 3' and 5' ends of the RNA, and the adapter-ligated RNA was reverse transcribed into single-stranded cDNA. The RNA 3' adapter was designed to target miRNAs and other small RNAs that have a 3' hydroxyl group resulting from enzymatic cleavage by Dicer or other RNA processing enzymes. The cDNA was then amplified by PCR, using a common primer and a primer containing one of 12 index sequences. The introduction of the six-base index tag at the PCR step allowed multiplexed sequencing of different samples in a single lane of a flowcell. A 0.5% PhiX spikein was also added in all lanes for quality control. Each multiplexed library was hybridized to one lane of the four 8-lane High-Output single-read flow cells on a cBot Cluster Generation System™ (Illumina) using TruSeq Single-Read Cluster Kit™ (Illumina). The clustered flowcell was loaded onto a HiSeq 2000 sequencer for a multiplexed sequencing run, which consists of a standard 36-cycle sequencing read with the addition of a 7-cycle index read.

miRNA Alignment and Quality Control

To estimate miRNA expression, a small RNA sequencing pipeline described previously was used (10). Briefly, the 30 adapter sequence was trimmed using the FASTX toolkit. Reads longer than 15 nt were aligned to hg19 using Bowtie™ v0.12.7 (11) allowing up to one mismatch and alignment to up to 10 genomic locations. miRNA expression was quantified by counting the number of reads aligning to mature miRNA loci (miRBase v20) using Bedtools™ v2.9.0 (12, 13). miRNA counts within each sample were normalized to log 2RPM values by adding a pseudocount of one to each miRNA, dividing by the total number of reads that aligned to all miRNA loci within that sample, multiplying by $1 \times 10^6$, and then applying a log$_2$ transformation (10). The log$_2$RPM expression values follow a normal distribution by an Anderson-Darling test (P=$2.2 \times 10^{-16}$; ref 14).

Next, the distribution of read lengths present in each sample was examined to ensure that the sequences observed were of the proper length for miRNA. The read length distribution ought to follow a normal distribution with a mean of 22 bases. samples whose distribution had an abundance of reads well below or above the mean of 22 bases (with less than one million reads aligned to 22 read length) were filtered out, indicating that the sample was not properly sequenced, the adapters were improperly trimmed, or the sample was of poor quality. Six such samples were removed, leaving 341 samples included in the downstream analysis. In addition, miRNA loci with a low number of aligned reads were removed (less than 20 on average). A total of 463 miRNA loci passed the filter and were included in the analysis. Finally, ComBat™ (15) was applied to normalize the miRNA expression in the three different batches. Large-scale variability in miRNA expression was examined by principal components analysis. No outlier samples were detected using the first two principal components, and there were no apparent global differences in miRNA expression between samples from AEGIS-1 and AEGIS-2 (data not shown).

Data Availability

Raw FASTQ files as well as the normalized miRNA expression data are available on Gene Expression Omnibus (GEO) under the GEO accession number GSE93284. mRNA data from Whitney and colleagues and Silvestri and colleagues was used (GSE66499; refs. 4, 5).

Differential Expression Analysis

To identify smoking-associated miRNAs, while correcting for covariates, an F test (anova R function; ref 16) was applied between a multiple linear regression (lm R function), with miRNA expression as the response variable, and smoking status, age, gender, cancer status, and pack-years as independent variables, and another multiple linear regression that did not include the smoking status as an independent variable.

Similarly, to identify miRNAs with cancer-associated expression patterns in the discovery cohort, while correcting for covariates, an F test was applied between a multiple linear regression, with miRNA expression as the response variable, and cancer status, age, gender, smoking status, and pack-years as independent variables, and another multiple linear regression that did not include the cancer status as an independent variable.

The P values were adjusted for FDR using Benjamini-Hochberg FDR (17) and are denoted with q-value.

Identifying miRNA-mRNA Relationships

The correlations between the differentially expressed miRNAs and their targets as predicted in the TargetScan database (18) were analyzed. The conserved targets as defined in TargetScan 5 and 6 (8mer 0.8; 7mer-m8 1.3; 7mer-1A 1.6) were included. The probability of conserved targeting (19) has the advantage of identifying targeting interactions that are not only more likely to e effective but also those that are more likely to be consequential. Correlation coefficients were calculated using Pearson product moment coefficient. For each miRNA, the resulting distribution of correlation coefficients were compared with the distribution of correlation coefficients between the miRNA and all the genes that have not been predicted to be targeted by it in TargetScan, using the Kolmogorov-Smirnov test.

Next, it was tested whether the negatively correlated targets (correlation FDR<0.1) of each differentially expressed miRNA were enriched among the genes whose expression is associated with cancer status by gene set enrichment analysis (GSEA; ref 20). For this enrichment analysis, genes were ranked by the t statistic of a multiple linear regression, with miRNA expression as the response variable, and cancer status, age, gender, smoking status, and pack-years as independent variables.

Incorporating miRNA Expression into the mRNA Classifier

First, the prediction score of the mRNA classifier was calculated (4, 5). Then, for each cancer-associated miRNA, the mRNA classifier score was integrated with the miRNA's expression using logistic regression (glmnet R package). The coefficients of the logistic regression, corresponding to the intercept ($\alpha_0$=1.8480041), weight of the classifier score ($\alpha_1$=4.3879703), and weight of the miRNA's expression ($\alpha_2$=−0.3724577), were determined in the discovery set, and the performance of the fully specified model was evaluated in the independent test set samples. Classification performance was assessed using the area under the receiver operating characteristic curve (ROC AUC). The statistical significance of the AUC improvement was computed by DeLong test (21) from the pROC R package (22).

Results

Patient Population miRNA expression was profiled via small RNA sequencing for 347 patients (194 cancer-positive and 153 cancer-negative subjects) participating in the AEGIS-1 and AEGIS-2 trials. Of the 347 miRNA samples, 341 passed the sequencing quality control filter (10). The characteristics of the discovery set (138 samples) and the test set (203 samples) are shown in Table 2. Except for cancer status, the other clinical variables are not significantly different between the training and test sets. Significant associations were also found between cancer status and age and lesion size in the discovery set and with pack-years and lesion size in the test set (data not shown).

Identifying Smoking-Associated miRNAs in Airway Epithelium

Previous work has shown that cigarette smoke creates a molecular field of injury throughout the airway, and specifically that miRNA expression is altered with tobacco smoke exposure (9, 23-28). The ability to detect miRNAs with smoking status-associated expression was used as a positive control for the quality of the miRNA expression data. A set of 28 miRNAs was previously identified as modulators of smoking-related gene expression changes in airway epithelium (9), with most of them (n=23) being downregulated in current smokers compared with never smokers. It was found that the miRNAs previously identified as being repressed by smoking were significantly enriched among the miRNAs that were most downregulated in current smokers from AEGIS (GSEA q<0.001), as shown in FIG. 1.

In addition, using the data described herein, significantly differentially expressed miRNAs between current and former smokers were identified by linear regression. 135 smoking-associated miRNAs were found by P<0.05 (Table 4). The top 30 differentially expressed miRNAs in the discovery set (q<0.01) are shown in Table 4. Among these, there were found miRNAs whose expression has been previously associated with smoking, such as miR-218, miR-365, miR-30a, and miR-99a (9).

The relationship between bronchial miRNA expression and other potentially relevant clinical variables, such as gender, age, and pack-years were also analyzed (Tables 5-7).

It was found that in addition to smoking status, gender is also associated with miRNA expression (85 differentially expressed miRNAs, P<0.05).

Cancer-Associated miRNA Alterations in the Bronchial Airway Epithelium

Using the discovery set (n=138), 42 miRNAs were identified that showed differential expression between patients with and without cancer by linear regression at a liberal P value threshold of P<0.05 (Table 8). Of these, four miRNA isoforms showed evidence of differential expression at FDR<0.2 (P<0.002). These four are: miR-146a-5p, miR-324-5p, miR-223-3p, and miR-223-5p. The expression profiles of these four miRNAs are shown in FIGS. 2A-2D. Consistent with the potential for these miRNAs to function as tumor suppressors, it was find that the four differentially expressed miRNA isoforms are downregulated in the bronchial airway of patients with lung cancer.

Cancer-Associated miRNAs as Potential Regulators of the Airway Gene Expression Alterations miRNAs often lead to the degradation of the mRNAs to which they bind. Therefore, it was sought to determine whether the expression of these miRNAs was negatively correlated with the expression of their gene targets. It was found that the distribution of the correlation coefficients of each cancer-associated miRNA and its predicted mRNA targets (binding site predicted targets from TargetScan) is significantly more negative than the distribution of correlation coefficients for nontarget genes ($P<10^{-9}$ for each miRNA; FIGS. 3A-3D).

It was next sought to assess whether bronchial miRNA expression could add to the performance of an mRNA biomarker for lung cancer which was previously identified (4). Using the training set samples, logistic regression was used to build five cancer prediction models: one model contained the mRNA biomarker score alone, the other four models contained the mRNA biomarker score in combination with one of the four miRNAs identified as having significant cancer-associated expression.

Next, the ROC curve AUC of the mRNA biomarker was compared alone with the four miRNA-containing models using a test set (Table 2) comprised of AEGIS1 and AEGIS-2 samples that are independent of the AEGIS-1 samples used to identify the four miRNAs with cancer-associated expression and independent of the samples used to develop the mRNA biomarker. It was found that adding miR-146a-5p to the mRNA biomarker significantly improved the AUC in the test set, from 0.66 to 0.71 (P=0.025). The AUC of biomarkers incorporating either miR-324-5p or either of the two isoforms of miR-223 was not significantly different than the AUC of the mRNA biomarker alone (P>0.25) in the test set. The performance metrics of each miRNA combined with the mRNA biomarker are provided in Table 9.

Discussion

Bronchial airway gene expression differences between patients with and without lung cancer can be used as a biomarker with clinical utility in the setting of patients with inconclusive results following bronchoscopy for suspect lung cancer (4-6). It was determined herein that miRNA expression was also be altered in the normal-appearing epithelium of the mainstem bronchus, whether these miRNA expression differences play a role in regulating the observed gene expression differences, and that lung cancer-associated miRNAs have the potential to aid in the detection of disease.

Described herein are four miRNA isoforms (miR-146a-5p, miR-324-5p, miR-223-3p, and miR-223-5p) that have altered expression in the airway epithelium of patients with lung cancer. That all four miRNAs have decreased expression in the bronchial airway of lung cancer patients is consistent with prior studies that have found miRNAs with cancer-specific expression, mostly downregulated, in tumors compared with normal tissue (34).

Although miRNA expression differences have been well documented in tumors, these results are the first to demonstrate altered expression of not just these cancer-related miRNAs, but any miRNA in the bronchial airway of lung cancer patients. The expression of mRNAs that are predicted targets of these miRNAs is significantly negatively correlated, suggesting that the expression of downstream genes is induced as a consequence of the cancer-dependent loss of miRNA expression.

Each differentially expressed miRNA's ability to enhance the performance of an mRNA-based lung cancer biomarker was assessed and it was found that miR-146a-5p significantly improves performance. One possible explanation for why miR-223-3p and miR-223-5p did not improve biomarker performance is that one of their targets (SNCA) is already a component of the mRNA classifier; thus, miR-223 expression might be substantially redundant with SNCA expression levels. If this hypothesis is correct, it would suggest that miR-146a adds to the biomarker's performance because the mRNA biomarker does not already capture miR-146a-related expression information.

In this study, demonstrated for the first time is the presence of an miRNA field of injury in the bronchial airway for lung cancer.

REFERENCES

1. Tukey M H, Wiener R S. Population-based estimates of transbronchial lung biopsy utilization and complications. Respir Med 2012; 106:1559-65.
2. Rivera M P, Mehta A C, Wahidi M M. Establishing the diagnosis of lung cancer: Diagnosis and management of lung cancer, 3rd ed: American College of Chest Physicians evidence-based clinical practice guidelines. Chest 2013; 143:e142S-65S.
3. Wang Memoli J S, Nietert P J, Silvestri G A. Meta-analysis of guided bronchoscopy for the evaluation of the pulmonary nodule. Chest 2012; 142:385-93.
4. Whitney D H, Elashoff M R, Porta-Smith K, Gower A C, Vachani A, Ferguson J S, et al. Derivation of a bronchial genomic classifier for lung cancer in a prospective study of patients undergoing diagnostic bronchoscopy. BMC Med Genomics 2015; 8:18.
5. Silvestri G A, Vachani A, Whitney D, Elashoff M, Smith K P, Ferguson J S, et al. A bronchial genomic classifier for the diagnostic evaluation of lung cancer. N Engl J Med 2015; 373:243-51.
6. Spira A, Beane J E, Shah V, Steiling K, Liu G, Schembri F, et al. Airway epithelial gene expression in the diagnostic evaluation of smokers with suspect lung cancer. Nat Med 2007; 13:361-6.
7. Etheridge A, Lee I, Hood L, Galas D, Wang K. Extracellular microRNA: a new source of biomarkers. Mutat Res 2011; 717:85-90.
8. Perdomo C, Campbell J D, Gerrein J, Tellez C S, Garrison C B, Walser T C, et al. MicroRNA 4423 is a primate-specific regulator of airway epithelial cell differentiation and lung carcinogenesis. Proc Natl Acad Sci USA 2013; 110:18946-51.
9. Schembri F, Sridhar S, Perdomo C, Gustafsond A M, Zhangd X, Ergun A, et al. MicroRNAs as modulators of smoking-induced gene expression changes in human airway epithelium. Proc Natl Acad Sci USA 2009; 106: 2319-24.
10. Campbell J D, Liu G, Luo L, Xiao J, Gerrein J, Juan-Guardela B, et al. Assessment of microRNA differential expression and detection in multiplexed small RNA sequencing data. RNA 2015; 21:164-71.
11. Langmead B, Trapnell C, Pop M, Salzberg S L. Ultrafast and memory efficient alignment of short DNA sequences to the human genome. Genome Biol 2009; 10:R25.
12. Griffiths-Jones S. The microRNA Registry. Nucleic Acids Res 2004; 32: D109-11.
13. Quinlan A R, Hall I M. BEDTools: a flexible suite of utilities for comparing genomic features. Bioinformatics 2010; 26:841-2.
14. Thode H C. Testing for normality. New York, N.Y.: CRC Press; 2002.
15. Johnson W E, Li C, Rabinovic A. Adjusting batch effects in microarray expression data using empirical Bayes methods. Biostatistics 2007; 8:118-27.
16. Chambers J. Linear models. Pacific Grove, Calif.: Wadsworth & Brooks/Cole; 1992.
17. Benjamini Y, Hochberg Y. Controlling the false discovery rate: a practical and powerful approach to multiple testing. J R Stat Soc Series B Methodol 1995; 57:289-300.
18. Lewis B P, Burge C B, Bartel D P. Conserved seed pairing, often flanked by adenosines, indicates that thousands of human genes are microRNA targets. Cell 2005; 120:15-20.
19. Friedman R C, Farh K K-H, Burge C B, Bartel D P. Most mammalian mRNAs are conserved targets of microRNAs. Genome Res 2008; 19:92-105.
20. Subramanian A, Tamayo P, Mootha V K, Mukherjee S, Ebert B L, Gillette M A, et al. Gene set enrichment analysis: a knowledge-based approach for interpreting genome-wide expression profiles. Proc Natl Acad Sci USA 2005; 102:15545-50.
21. DeLong E R, DeLong D M, Clarke-Pearson D L. Comparing the Areas under two or more correlated receiver operating characteristic curves: a nonparametric approach. Biometrics 1988; 44:837.
22. Robin X, Turck N, Hainard A, Tiberti N, Lisacek F, Sanchez J C, et al. pROC: an open-source package for R and Sb to analyze and compare ROC curves. BMC Bioinformatics 2011; 12:77.
23. Powell C A, Klares S, O'Connor G, Brody J S. Loss of heterozygosity in epithelial cells obtained by bronchial brushing: clinical utility in lung cancer. Clin Cancer Res 1999; 5:2025-34.
24. Wistuba I I, Lam S, Behrens C, Virmani A K, Fong K M, LeRiche J, et al. Molecular damage in the bronchial epithelium of current and former smokers. J Natl Cancer Inst 1997; 89:1366-73.
25. Franklin W A, Gazdar A F, Haney J, Wistuba I I, La Rosa F G, Kennedy T, et al. Widely dispersed p53 mutation in respiratory epithelium. A novel mechanism for field carcinogenesis. J Clin Invest 1997; 100:2133-7.
26. Guo M, House M G, Hooker C, Han Y, Heath E, Gabrielson E, et al. Promoter hypermethylation of resected bronchial margins: a field defect of changes? Clin Cancer Res 2004; 10:5131-6.
27. Miyazu Y M. Telomerase expression in noncancerous bronchial epithelia is a possible marker of early development of lung cancer. Cancer Res 2005; 65:9623-7.
28. Spira A, Beane J, Shah V, Liu G, Schembri F, Yang X, et al. Effects of cigarette smoke on the human airway epithelial cell transcriptome. Proc Natl Acad Sci USA 2004; 101:10143-8.
29. Chen G, Umelo I A, Lv S, Teugels E, Fostier K, Kronenberger P, et al. miR146a inhibits cell growth, cell migration and induces apoptosis in nonsmall cell lung cancer cells. PLoS One 2013; 8:e60317.
30. Labbaye C, Testa U. The emerging role of MIR-146A in the control of hematopoiesis, immune function and cancer. J Hematol Oncol 2012; 5:13.
31. Li G, Liu Y, Su Z, Ren S, Zhu G, Tian Y, et al. MicroRNA-324-3p regulates nasopharyngeal carcinoma radio resistance by directly targeting WNT2B. Eur J Cancer 2013; 49:2596-607.
32. Nian W, Ao X, Wu Y, Huang Y, Shao J, Wang Y, et al. miR-223 functions as a potent tumor suppressor of the Lewis lung carcinoma cell line by targeting insulin-like growth factor-1 receptor and cyclin-dependent kinase 2. Oncol Lett 2013; 6:359-66.
33. Huang D W, Sherman B T, Lempicki R A. Systematic and integrative analysis of large gene lists using DAVID bioinformatics resources. Nat Protoc 2009; 4:44-57.
34. Lu J, Getz G, Miska E A, Alvarez-Saavedra E, Lamb J, Peck D, et al. MicroRNA expression profiles classify human cancers. Nature 2005; 435:834-8.
35. Kumaraswamy E, Wendt K L, Augustine L A, Stecklein S R, Sibala E C, Li D, et al. BRCA1 regulation of epidermal growth factor receptor (EGFR) expression in human breast cancer cells involves micro-RNA-146a and is critical for its tumor suppressor function. Oncogene 2015; 34:4333-46.
36. Bhaumik D, Scott G K, Schokrpur S, Patil C K, Orjalo A V, Rodier F, et al. MicroRNAs miR-146a/b negatively modulate the senescence-associated inflammatory mediators IL-6 and IL-8. Aging 2009; 1:402-11.
37. Mao X, Kikani C K, Riojas R A, Langlais P, Wang L, Ramos F J, et al. APPL1 binds to adiponectin receptors and mediates adiponectin signalling and function. Nat Cell Biol 2006; 8:516-23.
38. Buechler C, Wanninger J, Neumeier M. Adiponectin receptor binding proteins—recent advances in elucidating adiponectin signalling pathways. FEBS Lett 2010; 584: 4280-6.
39. Singh B, Reddy P G, Goberdhan A, Walsh C, Dao S, Ngai I, et al. p53 regulates cell survival by inhibiting PIK3CA in squamous cell carcinomas. Genes Dev 2002; 16:984-93.
40. Gustafson A M, Soldi R, Anderlind C, Scholand M B, Qian J, Zhang X, et al. Airway PI3K pathway activation is an early and reversible event in lung cancer development. Sci Transl Med 2010; 2:26ra25.

TABLE 3

Patient demographics stratified by cancer status. The association of cancer with gender, smoking status and nodule size were computing using a Fisher's exact test; the association of cancer with age and cumulative smoke exposure were computed using a Student's t-test; n indicates number of patients with clinical data available; SD indicates standard deviation.

| | | Discovery set n = 138 | | | Test set n = 203 | | |
|---|---|---|---|---|---|---|---|
| | | Lung Cancer n = 88 | Benign n = 50 | p | Lung Cancer n = 103 | Benign n = 100 | p |
| Gender | Females | 25 | 37 | 0.84 | 38 | 46 | 0.2 |
| | Males | 63 | 13 | | 65 | 54 | |
| Age (SD; n) | | 61 (10; 88) | 56 (13; 50) | 0.01 | 60 (9; 103) | 58 (12; 100) | 0.29 |
| Smoking | Current | 32 | 14 | 0.35 | 47 | 41 | 0.57 |
| | Former | 56 | 36 | | 56 | 59 | |
| Cumulative Smoke Exposure - pack-yr. (SD; n) | | 38 (22; 88) | 33 (27; 49) | 0.2 | 40 (28; 102) | 32 (30; 97) | 0.05 |
| Race | White | 69 | 40 | 0.98 | 74 | 75 | 0.8 |
| | Black | 15 | 9 | | 26 | 20 | |
| | Unknown | 4 | 1 | | 3 | 5 | |
| Lesion Size | <3 cm | 30 | 22 | $4 \cdot 10^{-4}$ | 20 | 51 | $8 \cdot 10^{-14}$ |
| | >=3 cm | 47 | 11 | | 73 | 18 | |
| | Infiltrate | 4 | 11 | | 6 | 25 | |
| | Unknown | 7 | 6 | | 4 | 6 | |

TABLE 4

Smoking associated microRNAs (p < 0.05)

| miRBase ID | microRNA name | p-value | t-statistic | Direction in current smokers |
|---|---|---|---|---|
| MI0000767_MIMAT0000710 | hsa-miR-365a-3p | 6.99E−14 | 8.384407 | UP |
| MI0000769_MIMAT0022834 | hsa-miR-365b-3p | 7.00E−14 | 8.384203 | UP |
| MI0005416_MIMAT0004284 | hsa-miR-675-5p | 7.43E−12 | 7.527167 | UP |
| MI0000289_MIMAT0000270 | hsa-miR-181a-3p | 1.97E−11 | 7.344121 | UP |
| MI0014228_MIMAT0015066 | hsa-miR-3065-5p | 2.92E−11 | 7.269376 | UP |
| MI0000294_MIMAT0000275 | hsa-miR-218-5p | 5.99E−11 | −7.13266 | DOWN |
| MI0000295_MIMAT0000275 | hsa-miR-218-5p | 6.17E−11 | −7.12678 | DOWN |
| MI0014228_MIMAT0015378 | hsa-miR-3065-3p | 8.02E−11 | 7.076626 | UP |
| MI0000683_MIMAT0000257 | hsa-miR-181b-5p | 9.07E−11 | 7.053075 | UP |
| MI0000270_MIMAT0000257 | hsa-miR-181b-5p | 9.43E−11 | 7.04563 | UP |
| MI0003137_MIMAT0002819 | hsa-miR-193b-3p | 3.94E−10 | 6.768818 | UP |
| MI0000783_MIMAT0000728 | hsa-miR-375 | 2.92E−07 | 5.408163 | UP |
| MI0000269_MIMAT0000256 | hsa-miR-181a-5p | 1.63E−06 | 5.022647 | UP |
| MI0000289_MIMAT0000256 | hsa-miR-181a-5p | 1.63E−06 | 5.022619 | UP |
| MI0003782_MIMAT0006789 | hsa-miR-1468 | 1.09E−05 | −4.57523 | DOWN |
| MI0000254_MIMAT0004550 | hsa-miR-30c-2-3p | 1.17E−05 | −4.55862 | DOWN |
| MI0003610_MIMAT0003266 | hsa-miR-598 | 2.26E−05 | 4.396201 | UP |
| MI0005543_MIMAT0004927 | hsa-miR-708-3p | 2.89E−05 | 4.334139 | UP |
| MI0005543_MIMAT0004926 | hsa-miR-708-5p | 6.18E−05 | 4.140067 | UP |
| MI0000089_MIMAT0000089 | hsa-miR-31-5p | 9.02E−05 | 4.040998 | UP |
| MI0000078_MIMAT0004495 | hsa-miR-22-5p | 9.43E−05 | 4.02934 | UP |
| MI0000088_MIMAT0000088 | hsa-miR-30a-3p | 0.000115 | −3.97679 | DOWN |
| MI0000269_MIMAT0004558 | hsa-miR-181a-2-3p | 0.000137 | −3.93045 | DOWN |
| MI0000737_MIMAT0001620 | hsa-miR-200a-5p | 0.000146 | 3.912748 | UP |
| MI0000273_MIMAT0004560 | hsa-miR-183-3p | 0.000157 | 3.893655 | UP |
| MI0000098_MIMAT0000095 | hsa-miR-96-5p | 0.000289 | 3.724799 | UP |
| MI0000101_MIMAT0000097 | hsa-miR-99a-5p | 0.000291 | −3.72306 | DOWN |
| MI0000273_MIMAT0000261 | hsa-miR-183-5p | 0.000306 | 3.7089 | UP |
| MI0003139_MIMAT0002411 | hsa-miR-181d | 0.000411 | −3.62574 | DOWN |
| MI0000078_MIMAT0000077 | hsa-miR-22-3p | 0.000626 | 3.505042 | UP |
| MI0000737_MIMAT0000682 | hsa-miR-200a-3p | 0.000845 | 3.416487 | UP |
| MI0000746_MIMAT0004678 | hsa-miR-99b-3p | 0.000904 | −3.39641 | DOWN |
| MI0003820_MIMAT0003884 | hsa-miR-454-5p | 0.000906 | −3.39591 | DOWN |
| MI0003205_MIMAT0002888 | hsa-miR-532-5p | 0.000947 | −3.38262 | DOWN |
| MI0005545_MIMAT0004929 | hsa-miR-190b | 0.000975 | −3.37397 | DOWN |
| MI0016436_MIMAT0018204 | hsa-miR-676-3p | 0.001084 | −3.34211 | DOWN |
| MI0000081_MIMAT0000080 | hsa-miR-24-3p | 0.001205 | 3.310141 | UP |
| MI0000064_MIMAT0000064 | hsa-let-7c | 0.001216 | −3.30728 | DOWN |
| MI0000080_MIMAT0000080 | hsa-miR-24-3p | 0.001217 | 3.307088 | UP |
| MI0000470_MIMAT0004603 | hsa-miR-125b-2-3p | 0.001225 | −3.30498 | DOWN |
| MI0014186_MIMAT0015032 | hsa-miR-3158-3p | 0.001507 | −3.24164 | DOWN |
| MI0014187_MIMAT0015032 | hsa-miR-3158-3p | 0.001534 | −3.23617 | DOWN |

TABLE 4-continued

Smoking associated microRNAs (p < 0.05)

| miRBase ID | microRNA name | p-value | t-statistic | Direction in current smokers |
|---|---|---|---|---|
| MI0000460_MIMAT0004600 | hsa-miR-144-5p | 0.002046 | −3.14643 | DOWN |
| MI0005562_MIMAT0004951 | hsa-miR-887 | 0.002052 | 3.145495 | UP |
| MI0016010_MIMAT0018000 | hsa-miR-23c | 0.002269 | 3.113702 | UP |
| MI0001733_MIMAT0001636 | hsa-miR-452-3p | 0.002611 | 3.068962 | UP |
| MI0000079_MIMAT0000078 | hsa-miR-23a-3p | 0.003471 | 2.976788 | UP |
| MI0000301_MIMAT0000281 | hsa-miR-224-5p | 0.003558 | 2.968621 | UP |
| MI0000439_MIMAT0000418 | hsa-miR-23b-3p | 0.003769 | 2.949658 | UP |
| MI0002470_MIMAT0002177 | hsa-miR-486-5p | 0.003934 | −2.93552 | DOWN |
| MI0000805_MIMAT0004694 | hsa-miR-342-5p | 0.003953 | −2.93395 | DOWN |
| MI0000077_MIMAT0004494 | hsa-miR-21-3p | 0.004101 | 2.921693 | UP |
| MI0003591_MIMAT0003249 | hsa-miR-584-5p | 0.00437 | −2.90054 | DOWN |
| MI0000750_MIMAT0000082 | hsa-miR-26a-5p | 0.004811 | −2.86833 | DOWN |
| MI0000083_MIMAT0000082 | hsa-miR-26a-5p | 0.004813 | −2.86818 | DOWN |
| MI0006415_MIMAT0005929 | hsa-miR-1275 | 0.004879 | −2.86359 | DOWN |
| MI0003581_MIMAT0003239 | hsa-miR-574-3p | 0.005154 | 2.845097 | UP |
| MI0000441_MIMAT0004589 | hsa-miR-30b-3p | 0.005343 | −2.83292 | DOWN |
| MI0000234_MIMAT0000222 | hsa-miR-192-5p | 0.005851 | −2.80193 | DOWN |
| MI0000448_MIMAT0000425 | hsa-miR-130a-3p | 0.005886 | −2.79989 | DOWN |
| MI0000082_MIMAT0000081 | hsa-miR-25-3p | 0.005893 | −2.7995 | DOWN |
| MI0000077_MIMAT0000076 | hsa-miR-21-5p | 0.006117 | 2.786672 | UP |
| MI0001733_MIMAT0001635 | hsa-miR-452-5p | 0.006251 | 2.779215 | UP |
| MI0000272_MIMAT0000259 | hsa-miR-182-5p | 0.006668 | 2.756908 | UP |
| MI0001729_MIMAT0001631 | hsa-miR-451a | 0.00711 | −2.73462 | DOWN |
| MI0000089_MIMAT0004504 | hsa-miR-31-3p | 0.007343 | 2.72339 | UP |
| MI0003589_MIMAT0003247 | hsa-miR-582-5p | 0.007882 | 2.69853 | UP |
| MI0000748_MIMAT0000691 | hsa-miR-130b-3p | 0.008389 | 2.676552 | UP |
| MI0000088_MIMAT0000087 | hsa-miR-30a-5p | 0.008469 | −2.67318 | DOWN |
| MI0000736_MIMAT0004674 | hsa-miR-30c-1-3p | 0.008581 | −2.66855 | DOWN |
| MI0000272_MIMAT0000260 | hsa-miR-182-3p | 0.008731 | 2.662408 | UP |
| MI0000470_MIMAT0000423 | hsa-miR-125b-5p | 0.009243 | −2.64211 | DOWN |
| MI0000446_MIMAT0000423 | hsa-miR-125b-5p | 0.009518 | −2.63162 | DOWN |
| MI0000471_MIMAT0000445 | hsa-miR-126-3p | 0.009523 | −2.63144 | DOWN |
| MI0003589_MIMAT0004797 | hsa-miR-582-3p | 0.010005 | 2.613703 | UP |
| MI0000743_MIMAT0004677 | hsa-miR-34c-3p | 0.010512 | −2.59587 | DOWN |
| MI0000080_MIMAT0000079 | hsa-miR-24-1-5p | 0.010513 | 2.595842 | UP |
| MI0003834_MIMAT0003887 | hsa-miR-769-3p | 0.011142 | 2.574744 | UP |
| MI0000271_MIMAT0000258 | hsa-miR-181c-5p | 0.011176 | −2.57363 | DOWN |
| MI0000271_MIMAT0004559 | hsa-miR-181c-3p | 0.01136 | −2.5677 | DOWN |
| MI0000469_MIMAT0004602 | hsa-miR-125a-3p | 0.011383 | −2.56696 | DOWN |
| MI0017290_MIMAT0019731 | hsa-miR-4662a-5p | 0.011406 | −2.56622 | DOWN |
| MI0003575_MIMAT0004794 | hsa-miR-551b-5p | 0.012532 | −2.53171 | DOWN |
| MI0006406_MIMAT0005923 | hsa-miR-1269a | 0.013649 | −2.50014 | DOWN |
| MI0000434_MIMAT0004585 | hsa-let-7i-3p | 0.014389 | 2.480456 | UP |
| MI0000456_MIMAT0004597 | hsa-miR-140-3p | 0.014819 | −2.46945 | DOWN |
| MI0016789_MIMAT0018965 | hsa-miR-4446-3p | 0.016347 | −2.43247 | DOWN |
| MI0000764_MIMAT0000707 | hsa-miR-363-3p | 0.016384 | −2.43161 | DOWN |
| MI0015995_MIMAT0017982 | hsa-miR-3605-3p | 0.017059 | −2.41627 | DOWN |
| MI0003186_MIMAT0004775 | hsa-miR-502-3p | 0.017377 | −2.40923 | DOWN |
| MI0001519_MIMAT0001413 | hsa-miR-20b-5p | 0.018296 | −2.38951 | DOWN |
| MI0003657_MIMAT0020924 | hsa-miR-642a-3p | 0.018614 | −2.38289 | DOWN |
| MI0000812_MIMAT0004700 | hsa-miR-331-5p | 0.018661 | 2.381911 | UP |
| MI0002470_MIMAT0004762 | hsa-miR-486-3p | 0.019508 | −2.3648 | DOWN |
| MI0003190_MIMAT0004776 | hsa-miR-505-5p | 0.021653 | −2.32421 | DOWN |
| MI0000101_MIMAT0004511 | hsa-miR-99a-3p | 0.021731 | −2.3228 | DOWN |
| MI0000288_MIMAT0000269 | hsa-miR-212-3p | 0.02358 | 2.290676 | UP |
| MI0000253_MIMAT0000243 | hsa-miR-148a-3p | 0.023882 | 2.285637 | UP |
| MI0000107_MIMAT0000100 | hsa-miR-29b-3p | 0.02423 | 2.279899 | UP |
| MI0003184_MIMAT0002871 | hsa-miR-500a-3p | 0.024263 | −2.27936 | DOWN |
| MI0000105_MIMAT0000100 | hsa-miR-29b-3p | 0.024364 | 2.277713 | UP |
| MI0000732_MIMAT0000460 | hsa-miR-194-5p | 0.025292 | −2.26283 | DOWN |
| MI0000267_MIMAT0000254 | hsa-miR-10b-5p | 0.025327 | −2.26227 | DOWN |
| MI0000086_MIMAT0000085 | hsa-miR-28-5p | 0.026716 | 2.240894 | UP |
| MI0000791_MIMAT0000738 | hsa-miR-383 | 0.027841 | −2.22429 | DOWN |
| MI0000434_MIMAT0000415 | hsa-let-7i-5p | 0.029044 | −2.20717 | DOWN |
| MI0000488_MIMAT0000460 | hsa-miR-194-5p | 0.029417 | −2.20198 | DOWN |
| MI0005561_MIMAT0004949 | hsa-miR-877-5p | 0.030033 | 2.193535 | UP |
| MI0003639_MIMAT0004808 | hsa-miR-625-3p | 0.030715 | 2.184364 | UP |
| MI0000460_MIMAT0000436 | hsa-miR-144-3p | 0.032348 | −2.16311 | DOWN |
| MI0000812_MIMAT0000760 | hsa-miR-331-3p | 0.033042 | 2.154355 | UP |
| MI0016413_MIMAT0018183 | hsa-miR-3909 | 0.033468 | 2.149058 | UP |
| MI0000113_MIMAT0000103 | hsa-miR-106a-5p | 0.034881 | −2.13191 | DOWN |
| MI0000288_MIMAT0022695 | hsa-miR-212-5p | 0.035107 | 2.129219 | UP |
| MI0003685_MIMA10003339 | hsa-miR-421 | 0.036102 | 2.11756 | UP |
| MI0000439_MIMAT0004587 | hsa-miR-23b-5p | 0.03665 | 2.111253 | UP |
| MI0006358_MIMAT0005886 | hsa-miR-1297 | 0.036658 | −2.11116 | DOWN |

TABLE 4-continued

Smoking associated microRNAs (p < 0.05)

| miRBase ID | microRNA name | p-value | t-statistic | Direction in current smokers |
|---|---|---|---|---|
| MI0000462_MIMAT0000438 | hsa-miR-152 | 0.036967 | 2.107647 | UP |
| MI0006357_MIMA10005885 | hsa-miR-1295a | 0.037339 | −2.10344 | DOWN |
| MI0006394_MIMA10005911 | hsa-miR-1260a | 0.038609 | −2.08937 | DOWN |
| MI0005765_MIMAT0004984 | hsa-miR-941 | 0.03994 | 2.075042 | UP |
| MI0005763_MIMAT0004984 | hsa-miR-941 | 0.03994 | 2.075042 | UP |
| MI0003132_MIMAT0003161 | hsa-miR-493-3p | 0.040122 | −2.07311 | DOWN |
| MI0000342_MIMAT0000318 | hsa-miR-200b-3p | 0.041066 | 2.063223 | UP |
| MI0005530_MIMAT0002881 | hsa-miR-509-3p | 0.041551 | −2.05823 | DOWN |
| MI0005717_MIMAT0002881 | hsa-miR-509-3p | 0.041551 | −2.05823 | DOWN |
| MI0003196_MIMAT0002881 | hsa-miR-509-3p | 0.041551 | −2.05823 | DOWN |
| MI0016053_MIMAT0018073 | hsa-miR-3653 | 0.042775 | −2.04582 | DOWN |
| MI0000742_MIMAT0004676 | hsa-miR-34b-3p | 0.043272 | −2.04088 | DOWN |
| MI0000290_MIMAT0000271 | hsa-miR-214-3p | 0.044466 | −2.02918 | DOWN |
| MI0015825_MIMA10016847 | hsa-miR-378c | 0.045614 | 2.018188 | UP |
| MI0000481_MIMAT0000454 | hsa-miR-184 | 0.047471 | 2.000892 | UP |
| MI0000479_MIMAT0000451 | hsa-miR-150-5p | 0.048959 | −1.98744 | DOWN |
| MI0000094_MIMAT0000092 | hsa-miR-92a-3p | 0.049239 | −1.98495 | DOWN |
| MI0003195_MIMAT0002880 | hsa-miR-508-3p | 0.049502 | −1.98262 | DOWN |

TABLE 5

Gender associated microRNAs (p < 0.05)

| miRBase ID | microRNA name | p-value | t-statistic | Direction in males |
|---|---|---|---|---|
| MI0003591_MIMAT0003249 | hsa-miR-584-5p | 8.71E-05 | 4.050113 | UP |
| MI0006406_MIMAT0005923 | hsa-miR-1269a | 0.00038 | −3.64802 | DOWN |
| MI0000261_MIMAT0000250 | hsa-miR-139-5p | 0.000421 | 3.619431 | UP |
| MI0002470_MIMAT0002177 | hsa-miR-486-5p | 0.00051 | 3.564016 | UP |
| MI0002470_MIMAT0004762 | hsa-miR-486-3p | 0.000597 | 3.518597 | UP |
| MI0000764_MIMAT0000707 | hsa-miR-363-3p | 0.001246 | 3.299905 | UP |
| MI0000482_MIMAT0000455 | hsa-miR-185-5p | 0.001287 | 3.290067 | UP |
| MI0005767_MIMAT0004985 | hsa-miR-942 | 0.00245 | 3.089317 | UP |
| MI0001729_MIMAT0001631 | hsa-miR-451a | 0.00249 | 3.084152 | UP |
| MI0000267_MIMAT0000254 | hsa-miR-10b-5p | 0.003311 | 2.992199 | UP |
| MI0017878_MIMAT0021044 | hsa-miR-5010-3p | 0.003669 | 2.958545 | UP |
| MI0005524_MIMAT0004902 | hsa-miR-891a | 0.003731 | 2.95302 | UP |
| MI0000487_MIMAT0004614 | hsa-miR-193a-5p | 0.004155 | 2.917373 | UP |
| MI0000737_MIMAT0001620 | hsa-miR-200a-5p | 0.004183 | −2.91512 | DOWN |
| MI0003205_MIMAT0002888 | hsa-miR-532-5p | 0.00421 | 2.912991 | UP |
| MI0016005_MIMAT0017994 | hsa-miR-3615 | 0.004315 | 2.904792 | UP |
| MI0000460_MIMAT0004600 | hsa-miR-144-5p | 0.0044 | 2.898319 | UP |
| MI0000762_MIMAT0000705 | hsa-miR-362-5p | 0.004953 | 2.858559 | UP |
| MI0003132_MIMAT0003161 | hsa-miR-493-3p | 0.005383 | 2.830367 | UP |
| MI0000471_MIMAT0000445 | hsa-miR-126-3p | 0.00618 | 2.783127 | UP |
| MI0000113_MIMAT0000103 | hsa-miR-106a-5p | 0.00626 | 2.778729 | UP |
| MI0000743_MIMAT0000686 | hsa-miR-34c-5p | 0.008081 | −2.68977 | DOWN |
| MI0003184_MIMAT0002871 | hsa-miR-500a-3p | 0.008227 | 2.683471 | UP |
| MI0006359_MIMAT0005887 | hsa-miR-1299 | 0.008432 | 2.674752 | UP |
| MI0000482_MIMAT0004611 | hsa-miR-185-3p | 0.008837 | 2.658095 | UP |
| MI0000742_MIMAT0000685 | hsa-miR-34b-5p | 0.008861 | −2.65714 | DOWN |
| MI0003129_MIMAT0002809 | hsa-miR-146b-5p | 0.008881 | 2.656329 | UP |
| MI0000737_MIMAT0000682 | hsa-miR-200a-3p | 0.009483 | −2.63292 | DOWN |
| MI0000082_MIMAT0000081 | hsa-miR-25-3p | 0.009953 | 2.615567 | UP |
| MI0003583_MIMAT0003241 | hsa-miR-576-5p | 0.011609 | 2.559776 | UP |
| MI0000734_MIMAT0004672 | hsa-miR-106b-3p | 0.01165 | 2.55849 | UP |
| MI0003132_MIMAT0002813 | hsa-miR-493-5p | 0.011967 | 2.548663 | UP |
| MI0000461_MIMAT0000437 | hsa-miR-145-5p | 0.012154 | 2.542988 | UP |
| MI0014234_MIMA10015072 | hsa-miR-320e | 0.012943 | 2.519831 | UP |
| MI0000748_MIMAT0000691 | hsa-miR-130b-3p | 0.013366 | 2.507912 | UP |
| MI0000471_MIMAT0000444 | hsa-miR-126-5p | 0.013573 | 2.502228 | UP |
| MI0000459_MIMAT0000435 | hsa-miR-143-3p | 0.014702 | 2.472407 | UP |
| MI0000448_MIMAT0000425 | hsa-miR-130a-3p | 0.015185 | 2.460286 | UP |
| MI0000438_MIMAT0004586 | hsa-miR-15b-3p | 0.01567 | 2.448448 | UP |
| MI0000814_MIMAT0004701 | hsa-miR-338-5p | 0.015785 | 2.445691 | UP |
| MI0000342_MIMAT0000318 | hsa-miR-200b-3p | 0.01587 | −2.44367 | DOWN |
| MI0001519_MIMAT0001413 | hsa-miR-20b-5p | 0.016517 | 2.428529 | UP |
| MI0000300_MIMAT0004570 | hsa-miR-223-5p | 0.017687 | 2.402462 | UP |
| MI0000094_MIMAT0000092 | hsa-miR-92a-3p | 0.017863 | 2.398675 | UP |
| MI0000461_MIMAT0004601 | hsa-miR-145-3p | 0.018111 | 2.393409 | UP |
| MI0000434_MIMAT0000415 | hsa-let-7i-5p | 0.01864 | 2.382346 | UP |

TABLE 5-continued

Gender associated microRNAs (p < 0.05)

| miRBase ID | microRNA name | p-value | t-statistic | Direction in males |
|---|---|---|---|---|
| MI0000093_MIMAT0000092 | hsa-miR-92a-3p | 0.019155 | 2.37185 | UP |
| MI0000816_MIMAT0004703 | hsa-miR-335-3p | 0.019155 | 2.371841 | UP |
| MI0000438_MIMAT0000417 | hsa-miR-15b-5p | 0.020899 | 2.338061 | UP |
| MI0003129_MIMAT0004766 | hsa-miR-146b-3p | 0.021041 | 2.335417 | UP |
| MI0000281_MIMAT0000232 | hsa-miR-199a-3p | 0.021208 | 2.332323 | UP |
| MI0000282_MIMAT0004563 | hsa-miR-199b-3p | 0.02133 | 2.330082 | UP |
| MI0000242_MIMAT0000232 | hsa-miR-199a-3p | 0.021332 | 2.330055 | UP |
| MI0000115_MIMAT0000069 | hsa-miR-16-5p | 0.021953 | 2.318821 | UP |
| MI0000115_MIMAT0004518 | hsa-miR-16-2-3p | 0.022134 | 2.315603 | UP |
| MI0000070_MIMAT0000069 | hsa-miR-16-5p | 0.022163 | 2.315092 | UP |
| MI0005565_MIMAT0004954 | hsa-miR-543 | 0.023505 | 2.291934 | UP |
| MI0003772_MIMAT0010214 | hsa-miR-151b | 0.023652 | 2.289467 | UP |
| MI0000290_MIMAT0000271 | hsa-miR-214-3p | 0.025275 | 2.263094 | UP |
| MI0000778_MIMAT0000722 | hsa-miR-370 | 0.025438 | 2.260537 | UP |
| MI0003185_MIMAT0002872 | hsa-miR-501-5p | 0.026337 | 2.246644 | UP |
| MI0003667_MIMAT0003322 | hsa-miR-652-3p | 0.028277 | 2.218005 | UP |
| MI0000472_MIMAT0000446 | hsa-miR-127-3p | 0.031579 | 2.172998 | UP |
| MI0000460_MIMAT0000436 | hsa-miR-144-3p | 0.031737 | 2.170951 | UP |
| MI0000265_MIMAT0000252 | hsa-miR-7-5p | 0.031786 | 2.170322 | UP |
| MI0000264_MIMAT0000252 | hsa-miR-7-5p | 0.031836 | 2.169671 | UP |
| MI0000263_MIMAT0000252 | hsa-miR-7-5p | 0.032048 | 2.166942 | UP |
| MI0000255_MIMAT0000245 | hsa-miR-30d-5p | 0.033298 | −2.15116 | DOWN |
| MI0000749_MIMAT0000692 | hsa-miR-30e-5p | 0.033377 | −2.15018 | DOWN |
| MI0000790_MIMAT0000737 | hsa-miR-382-5p | 0.033437 | 2.14944 | UP |
| MI0000085_MIMAT0000084 | hsa-miR-27a-3p | 0.033468 | −2.14906 | DOWN |
| MI0000747_MIMAT0004679 | hsa-miR-296-3p | 0.034018 | 2.142316 | UP |
| MI0003186_MIMAT0004775 | hsa-miR-502-3p | 0.034607 | 2.135181 | UP |
| MI0003632_MIMA10003287 | hsa-miR-618 | 0.035611 | 2.123284 | UP |
| MI0000802_MIMAT0004692 | hsa-miR-340-5p | 0.036036 | −2.11833 | DOWN |
| MI0000090_MIMAT0004505 | hsa-miR-32-3p | 0.037585 | −2.10069 | DOWN |
| MI0000456_MIMAT0004597 | hsa-miR-140-3p | 0.038434 | 2.091286 | UP |
| MI0000457_MIMAT0004598 | hsa-miR-141-5p | 0.03844 | −2.09122 | DOWN |
| MI0000813_MIMAT0000762 | hsa-miR-324-3p | 0.038692 | 2.08846 | UP |
| MI0000786_MIMA10000731 | hsa-miR-378a-5p | 0.041886 | 2.054805 | UP |
| MI0015995_MIMAT0017982 | hsa-miR-3605-3p | 0.0445 | 2.028849 | UP |
| MI0000650_MIMAT0000617 | hsa-miR-200c-3p | 0.045047 | −2.02359 | DOWN |
| MI0020364_MIMAT0023712 | hsa-miR-6087 | 0.047024 | 2.005 | UP |
| MI0003127_MIMA10002808 | hsa-miR-511 | 0.049781 | 1.980159 | UP |
| MI0000458_MIMAT0000433 | hsa-miR-142-5p | 0.049834 | 1.979692 | UP |

TABLE 6

Age associated microRNAs (p < 0.05)

| miRBase ID | microRNA name | p-value | t-statistic | Direction with age increase |
|---|---|---|---|---|
| MI0000102_MIMAT0000098 | hsa-miR-100-5p | 0.004609 | 2.882752 | UP |
| MI0000681_MIMAT0000646 | hsa-miR-155-5p | 0.008066 | −2.69041 | DOWN |
| MI0000289_MIMAT0000256 | hsa-miR-181a-5p | 0.009424 | −2.63516 | DOWN |
| MI0000269_MIMAT0000256 | hsa-miR-181a-5p | 0.009427 | −2.63504 | DOWN |
| MI0000289_MIMAT0000270 | hsa-miR-181a-3p | 0.009663 | −2.62621 | DOWN |
| MI0005416_MIMAT0004284 | hsa-miR-675-5p | 0.012408 | −2.53539 | DOWN |
| MI0003195_MIMAT0002880 | hsa-miR-508-3p | 0.014651 | 2.473715 | UP |
| MI0000086_MIMAT0000085 | hsa-miR-28-5p | 0.016109 | −2.43802 | DOWN |
| MI0000683_MIMAT0000257 | hsa-miR-181b-5p | 0.016941 | −2.41891 | DOWN |
| MI0000270_MIMAT0000257 | hsa-miR-181b-5p | 0.01724 | −2.41225 | DOWN |
| MI0003198_MIMAT0002883 | hsa-miR-514a-3p | 0.024898 | 2.269085 | UP |
| MI0003200_MIMAT0002883 | hsa-miR-514a-3p | 0.024898 | 2.269085 | UP |
| MI0003199_MIMAT0002883 | hsa-miR-514a-3p | 0.024898 | 2.269085 | UP |
| MI0005767_MIMAT0004985 | hsa-miR-942 | 0.030666 | −2.18502 | DOWN |
| MI0003760_MIMAT0004819 | hsa-miR-671-3p | 0.032443 | −2.1619 | DOWN |
| MI0000542_MIMAT0000510 | hsa-miR-320a | 0.033491 | −2.14878 | DOWN |
| MI0000441_MIMAT0000420 | hsa-miR-30b-5p | 0.034698 | 2.134098 | UP |
| MI0003601_MIMAT0004800 | hsa-miR-550a-5p | 0.038568 | −2.08981 | DOWN |
| MI0003600_MIMAT0004800 | hsa-miR-550a-5p | 0.038664 | −2.08876 | DOWN |
| MI0000476_MIMAT0000430 | hsa-miR-138-5p | 0.041213 | −2.06171 | DOWN |
| MI0000458_MIMAT0000433 | hsa-miR-142-5p | 0.043524 | −2.03838 | DOWN |
| MI0000269_MIMAT0004558 | hsa-miR-181a-2-3p | 0.04365 | −2.03714 | DOWN |

TABLE 6-continued

Age associated microRNAs (p < 0.05)

| miRBase ID | microRNA name | p-value | t-statistic | Direction with age increase |
|---|---|---|---|---|
| MI0000764_MIMAT0000707 | hsa-miR-363-3p | 0.04401 | −2.03361 | DOWN |
| MI0000481_MIMAT0000454 | hsa-miR-184 | 0.045025 | 2.023794 | UP |
| MI0000115_MIMAT0004518 | hsa-miR-16-2-3p | 0.047756 | −1.99829 | DOWN |

TABLE 7

Pack-years (PY) associated microRNAs (p < 0.05)

| miRBase ID | microRNA name | p-value | t-statistic | Direction with PY increase |
|---|---|---|---|---|
| MI0000071_MIMAT0000071 | hsa-miR-17-3p | 0.011764 | −2.55466 | DOWN |
| MI0003183_MIMAT0002870 | hsa-miR-499a-5p | 0.016027 | −2.4397 | DOWN |
| MI0015997_MIMAT0017985 | hsa-miR-3607-3p | 0.019021 | 2.374323 | UP |
| MI0000300_MIMAT0004570 | hsa-miR-223-5p | 0.019299 | 2.368731 | UP |
| MI0000434_MIMAT0004585 | hsa-let-7i-3p | 0.020197 | −2.35112 | DOWN |
| MI0005544_MIMAT0004928 | hsa-miR-147b | 0.030047 | 2.193163 | UP |
| MI0000088_MIMAT0000088 | hsa-miR-30a-3p | 0.030984 | 2.180624 | UP |
| MI0019308_MIMAT0022494 | hsa-miR-5701 | 0.036403 | 2.113925 | UP |
| MI0019593_MIMAT0022494 | hsa-miR-5701 | 0.036403 | 2.113925 | UP |
| MI0000068_MIMAT0000067 | hsa-let-7f-5p | 0.037702 | 2.099219 | UP |
| MI0000067_MIMAT0000067 | hsa-let-7f-5p | 0.039373 | 2.080928 | UP |
| MI0003780_MIMAT0005794 | hsa-miR-1296 | 0.039909 | −2.0752 | DOWN |
| MI0000101_MIMAT0004511 | hsa-miR-99a-3p | 0.040476 | −2.06922 | DOWN |
| MI0000300_MIMAT0000280 | hsa-miR-223-3p | 0.04588 | 2.015523 | UP |

TABLE 8

Cancer associated microRNAs (p < 0.05)

| miRBase ID | microRNA name | p-value | t-statistic | Direction in cancer |
|---|---|---|---|---|
| MI0000813_MIMAT0000761 | hsa-miR-324-5p | 0.000649 | −3.49412 | DOWN |
| MI0000300_MIMAT0000280 | hsa-miR-223-3p | 0.000714 | −3.46634 | DOWN |
| MI0000477_MIMAT0000449 | hsa-miR-146a-5p | 0.000808 | −3.4298 | DOWN |
| MI0000300_MIMAT0004570 | hsa-miR-223-5p | 0.001586 | −3.22597 | DOWN |
| MI0003834_MIMAT0003887 | hsa-miR-769-3p | 0.002842 | −3.04179 | DOWN |
| MI0003632_MIMAT0003287 | hsa-miR-618 | 0.003085 | −3.01518 | DOWN |
| MI0000814_MIMAT0004701 | hsa-miR-338-5p | 0.005204 | −2.8418 | DOWN |
| MI0000286_MIMAT0000267 | hsa-miR-210 | 0.007292 | −2.72581 | DOWN |
| MI0001652_MIMAT0001545 | hsa-miR-450a-5p | 0.008086 | −2.68953 | DOWN |
| MI0000441_MIMAT0000420 | hsa-miR-30b-5p | 0.008275 | −2.68142 | DOWN |
| MI0003187_MIMAT0001545 | hsa-miR-450a-5p | 0.008425 | −2.67505 | DOWN |
| MI0000268_MIMAT0000255 | hsa-miR-34a-5p | 0.009728 | −2.62381 | DOWN |
| MI0003667_MIMAT0003322 | hsa-miR-652-3p | 0.013213 | −2.51217 | DOWN |
| MI0000114_MIMAT0000104 | hsa-miR-107 | 0.016073 | −2.43885 | DOWN |
| MI0000783_MIMAT0000728 | hsa-miR-375 | 0.018023 | 2.395261 | UP |
| MI0000080_MIMAT0000079 | hsa-miR-24-1-5p | 0.018845 | 2.378128 | UP |
| MI0005562_MIMAT0004951 | hsa-miR-887 | 0.020166 | −2.35195 | DOWN |
| MI0005544_MIMAT0004928 | hsa-miR-147b | 0.022438 | −2.31024 | DOWN |
| MI0000089_MIMAT0000089 | hsa-miR-31-5p | 0.022548 | −2.30832 | DOWN |
| MI0000735_MIMAT0004673 | hsa-miR-29c-5p | 0.022925 | −2.30179 | DOWN |
| MI0000813_MIMAT0000762 | hsa-miR-324-3p | 0.023499 | −2.29203 | DOWN |
| MI0000825_MIMAT0000772 | hsa-miR-345-5p | 0.024099 | −2.28205 | DOWN |
| MI0005531_MIMAT0004909 | hsa-miR-450b-5p | 0.026429 | −2.24524 | DOWN |
| MI0003834_MIMAT0003886 | hsa-miR-769-5p | 0.027019 | −2.23636 | DOWN |
| MI0000808_MIMAT0000756 | hsa-miR-326 | 0.027116 | −2.23493 | DOWN |
| MI0005762_MIMAT0004983 | hsa-miR-940 | 0.028261 | −2.21824 | DOWN |
| MI0000433_MIMAT0000414 | hsa-let-7g-5p | 0.029329 | −2.20319 | DOWN |
| MI0003589_MIMAT0003247 | hsa-miR-582-5p | 0.030653 | −2.1852 | DOWN |
| MI0000748_MIMAT0004680 | hsa-miR-130b-5p | 0.030991 | 2.180711 | UP |
| MI0000089_MIMAT0004504 | hsa-miR-31-3p | 0.03322 | −2.15213 | DOWN |
| MI0016902_MIMAT0019074 | hsa-miR-378i | 0.033939 | −2.14328 | DOWN |
| MI0003190_MIMAT0002876 | hsa-miR-505-3p | 0.039021 | −2.08488 | DOWN |
| MI0006384_MIMAT0005901 | hsa-miR-1249 | 0.039448 | −2.08028 | DOWN |
| MI0000298_MIMAT0000278 | hsa-miR-221-3p | 0.039583 | −2.07884 | DOWN |
| MI0014197_MIMAT0015041 | hsa-miR-1260b | 0.039908 | −2.07538 | DOWN |
| MI0014249_MIMAT0015085 | hsa-miR-3200-3p | 0.042866 | −2.04492 | DOWN |
| MI0001448_MIMAT0001343 | hsa-miR-425-3p | 0.044056 | −2.03317 | DOWN |

TABLE 8-continued

Cancer associated microRNAs (p < 0.05)

| miRBase ID | microRNA name | p-value | t-statistic | Direction in cancer |
|---|---|---|---|---|
| MI0017438_MIMAT0019963 | hsa-miR-4791 | 0.044608 | −2.02781 | DOWN |
| MI0003780_MIMAT0005794 | hsa-miR-1296 | 0.045033 | −2.02372 | DOWN |
| MI0017308_MIMAT0019761 | hsa-miR-4677-3p | 0.045417 | −2.02006 | DOWN |
| MI0000273_MIMAT0000261 | hsa-miR-183-5p | 0.045741 | 2.016984 | UP |
| MI0000283_MIMAT0000264 | hsa-miR-203a | 0.049459 | 1.983001 | UP |

TABLE 9

Biomarker performance in the test set

|  | AUC (95% CI) | Sens† | Spec† | NPV† | PPV† |
|---|---|---|---|---|---|
| mRNA biomarker | 0.66 (0.58-0.73) | 0.94 | 0.27 | 0.78 | 0.60 |
| mRNA biomarker + miR-146a-5p | 0.71* (0.64-0.78) | 0.93 | 0.33 | 0.83 | 0.59 |
| mRNA biomarker + miR-324-5p | 0.65 (0.57-0.72) | 0.94 | 0.23 | 0.79 | 0.55 |
| mRNA biomarker + miR-223-3p | 0.67 (0.60-0.75) | 0.96 | 0.27 | 0.87 | 0.58 |
| mRNA biomarker + miR-223-5p | 0.67 (0.60-0.75) | 0.95 | 0.26 | 0.84 | 0.57 |

(*significant increase in AUC compared to mRNA biomarker p < 0.05; †ROC-curve Operating Point set to 90% sensitivity in the training set)

```
human miR-146a-5p
                              (SEQ ID NO: 2)
ugagaacugaauuccauggguu human miR-324-5p
                              (SEQ ID NO: 4)
cgcauccccuagggcauuggugu
```

-continued

```
human miR-223-3p
                              (SEQ ID NO: 6)
ugucaguuugucaaauacccca human miR-223-5p
                              (SEQ ID NO: 7)
cguguauuugacaagcugaguu human miR-450b-5p
                              (SEQ ID NO: 9)
uuuugcaauauguuccugaaua human miR-221-3p
                              (SEQ ID NO: 11)
agcuacauugucugcuggguuuc human miR-505-3p
                              (SEQ ID NO: 13)
cgucaacacuugcugguuuccu human miR-582-5p
                              (SEQ ID NO: 15)
uuacaguuguucaaccaguuacu
```

What is claimed herein is:

1. A method of detecting a level of expression of miR-324-5p and at least 1 miRNA selected from the group consisting of:
   miR-450b-5p and miR-582-5p;
in a bronchial brushing or nose epithelial sample obtained from a subject.

2. The method of claim 1, wherein the level of expression is further detected for at least one miRNA selected from the group consisting of:
   miR-146a-5p, miR-223-3p, miR-223-5p, miR-221-3p, and miR-505-3p.

3. The method of claim 1, wherein the level of expression is further detected for at least two miRNAs selected from the group consisting of:
   miR-146a-5p, miR-223-3p, miR-223-5p, miR-221-3p, and miR-505-3p.

4. The method of claim 1, wherein the level of expression is further detected for at least three miRNAs selected from the group consisting of:
   miR-146a-5p, miR-223-3p, miR-223-5p, miR-221-3p, and miR-505-3p.

5. The method of claim 1, wherein the level of expression is further detected for at least four miRNAs selected from the group consisting of:
   miR-146a-5p, miR-223-3p, miR-223-5p, miR-221-3p, and miR-505-3p.

6. The method of claim 1, wherein the level of expression is further detected for:
   miR-146a-5p, miR-223-3p, miR-223-5p, miR-221-3p, and miR-505-3p.

7. The method of claim 2, wherein the level of expression is detected for at least miR-146a-5p, miR-324-5p, miR-223-3p, and miR-223-5p.

8. The method of claim 2, wherein the level of expression is detected for at least miR-146a-5p.

9. The method of claim 1, wherein the method further comprises detecting the expression level of one or more mRNAs.

10. The method of claim 1, wherein the expression level of no more than 100 miRNAs and/or mRNAs is detected.

* * * * *

SEQUENCE LISTING

```
<160> NUMBER OF SEQ ID NOS: 15

<210> SEQ ID NO 1
<211> LENGTH: 99
<212> TYPE: DNA
<213> ORGANISM: Homo sapiens

<400> SEQUENCE: 1
ccgatgtgta tcctcagctt tgagaactga attccatggg ttgtgtcagt gtcagacctc    60
tgaaattcag ttcttcagct gggatatctc tgtcatcgt                           99

<210> SEQ ID NO 2
<211> LENGTH: 22
<212> TYPE: RNA
<213> ORGANISM: Homo sapiens

<400> SEQUENCE: 2
ugagaacuga auuccauggg uu                                             22

<210> SEQ ID NO 3
<211> LENGTH: 83
<212> TYPE: DNA
<213> ORGANISM: Homo sapiens

<400> SEQUENCE: 3
ctgactatgc ctccccgcat ccctagggc attggtgtaa agctggagac ccactgcccc     60
```
aggtgctgct gggggttgta gtc                                         83

<210> SEQ ID NO 4
<211> LENGTH: 23
<212> TYPE: RNA
<213> ORGANISM: Homo sapiens

<400> SEQUENCE: 4
cgcauccccu agggcauugg ugu                                         23

<210> SEQ ID NO 5
<211> LENGTH: 110
<212> TYPE: DNA
<213> ORGANISM: Homo sapiens

<400> SEQUENCE: 5
cctggcctcc tgcagtgcca cgctccgtgt atttgacaag ctgagttgga cactccatgt  60
ggtagagtgt cagtttgtca aatacccaa gtgcggcaca tgcttaccag            110

<210> SEQ ID NO 6
<211> LENGTH: 22
<212> TYPE: RNA
<213> ORGANISM: Homo sapiens

<400> SEQUENCE: 6
ugucaguuug ucaaauaccc ca                                          22

<210> SEQ ID NO 7
<211> LENGTH: 22
<212> TYPE: RNA
<213> ORGANISM: Homo sapiens

<400> SEQUENCE: 7
cguguauuug acaagcugag uu                                          22

<210> SEQ ID NO 8
<211> LENGTH: 78
<212> TYPE: DNA
<213> ORGANISM: Homo sapiens

<400> SEQUENCE: 8
gcagaattat ttttgcaata tgttcctgaa tatgtaatat aagtgtattg ggatcatttt  60
gcatccatag ttttgtat                                               78

<210> SEQ ID NO 9
<211> LENGTH: 22
<212> TYPE: RNA
<213> ORGANISM: Homo sapiens

<400> SEQUENCE: 9
uuuugcaaua uguuccugaa ua                                          22

<210> SEQ ID NO 10
<211> LENGTH: 110
<212> TYPE: DNA
<213> ORGANISM: Homo sapiens

<400> SEQUENCE: 10
tgaacatcca ggtctggggc atgaacctgg catacaatgt agatttctgt gttcgttagg  60
caacagctac attgtctgct gggtttcagg ctacctggaa acatgttctc            110

```
<210> SEQ ID NO 11
<211> LENGTH: 23
<212> TYPE: RNA
<213> ORGANISM: Homo sapiens

<400> SEQUENCE: 11
agcuacauug ucugcugggu uuc                                           23

<210> SEQ ID NO 12
<211> LENGTH: 84
<212> TYPE: DNA
<213> ORGANISM: Homo sapiens

<400> SEQUENCE: 12
gatgcaccca gtgggggagc caggaagtat tgatgtttct gccagtttag cgtcaacact   60
tgctggtttc ctctctggag catc                                          84

<210> SEQ ID NO 13
<211> LENGTH: 22
<212> TYPE: RNA
<213> ORGANISM: Homo sapiens

<400> SEQUENCE: 13
cgucaacacu ugcugguuuc cu                                            22

<210> SEQ ID NO 14
<211> LENGTH: 98
<212> TYPE: DNA
<213> ORGANISM: Homo sapiens

<400> SEQUENCE: 14
atctgtgctc tttgattaca gttgttcaac cagttactaa tctaactaat tgtaactggt   60
tgaacaactg aacccaaagg gtgcaaagta gaaacatt                           98

<210> SEQ ID NO 15
<211> LENGTH: 23
<212> TYPE: RNA
<213> ORGANISM: Homo sapiens

<400> SEQUENCE: 15
uuacaguugu ucaaccaguu acu                                           23
```